(12) United States Patent
Romo et al.

(10) Patent No.: US 12,364,994 B2
(45) Date of Patent: Jul. 22, 2025

(54) AUTOMATED DEPOSITION OF MICROFILMS, SYSTEMS AND METHODS

(71) Applicant: Leviant, Inc., Hawthorne, NY (US)

(72) Inventors: Luis F. Romo, New York, NY (US); Wladyslaw Kowalski, Long Island City, NY (US); Audrey McNicholas, Long Island City, NY (US)

(73) Assignee: Leviant, Inc., Hawthorne, NY (US)

( * ) Notice: Subject to any disclaimer, the term of this patent is extended or adjusted under 35 U.S.C. 154(b) by 595 days.

(21) Appl. No.: 17/723,997

(22) Filed: Apr. 19, 2022

(65) Prior Publication Data

US 2022/0241806 A1 Aug. 4, 2022

Related U.S. Application Data

(63) Continuation of application No. PCT/US2020/056886, filed on Oct. 22, 2020.

(60) Provisional application No. 62/924,313, filed on Oct. 22, 2019.

(51) Int. Cl.
| | |
|---|---|
| *B05B 7/12* | (2006.01) |
| *B05B 1/30* | (2006.01) |
| *B05B 13/00* | (2006.01) |
| *B05D 1/02* | (2006.01) |

(52) U.S. Cl.
CPC .............. *B05B 7/1209* (2013.01); *B05B 1/30* (2013.01); *B05B 13/00* (2013.01); *B05D 1/02* (2013.01)

(58) Field of Classification Search
CPC .................................................... B05B 7/1209
See application file for complete search history.

(56) References Cited

U.S. PATENT DOCUMENTS

| | | |
|---|---|---|
| 6,257,510 B1 | 7/2001 | Schuck |
| 9,267,204 B2 | 2/2016 | Honma |
| 2012/0009248 A1 | 1/2012 | Truong-Le et al. |

OTHER PUBLICATIONS

International Search Report and Written Opinion in PCT International Application No. PCT/US2020/056886 mailed Mar. 2, 2021.

*Primary Examiner* — Albert M Navarro
*Assistant Examiner* — Mark Navarro
(74) *Attorney, Agent, or Firm* — Nixon Peabody LLP

(57) ABSTRACT

The implementations include a system configured to automatically deposit a variable film of an inoculant containing one or more pathogens, the system including: a base configured with a receptacle for a removable chamber; a liquid inlet receiver configured to provide the inoculant from a liquid inlet thereon to the removable chamber; a gas inlet configured to provide a pressurized gas from a gas tank to the removable chamber; and an adjustable nozzle configured to spray the inoculant from the liquid inlet and under the pressurized gas from the gas inlet.

30 Claims, 34 Drawing Sheets

1000

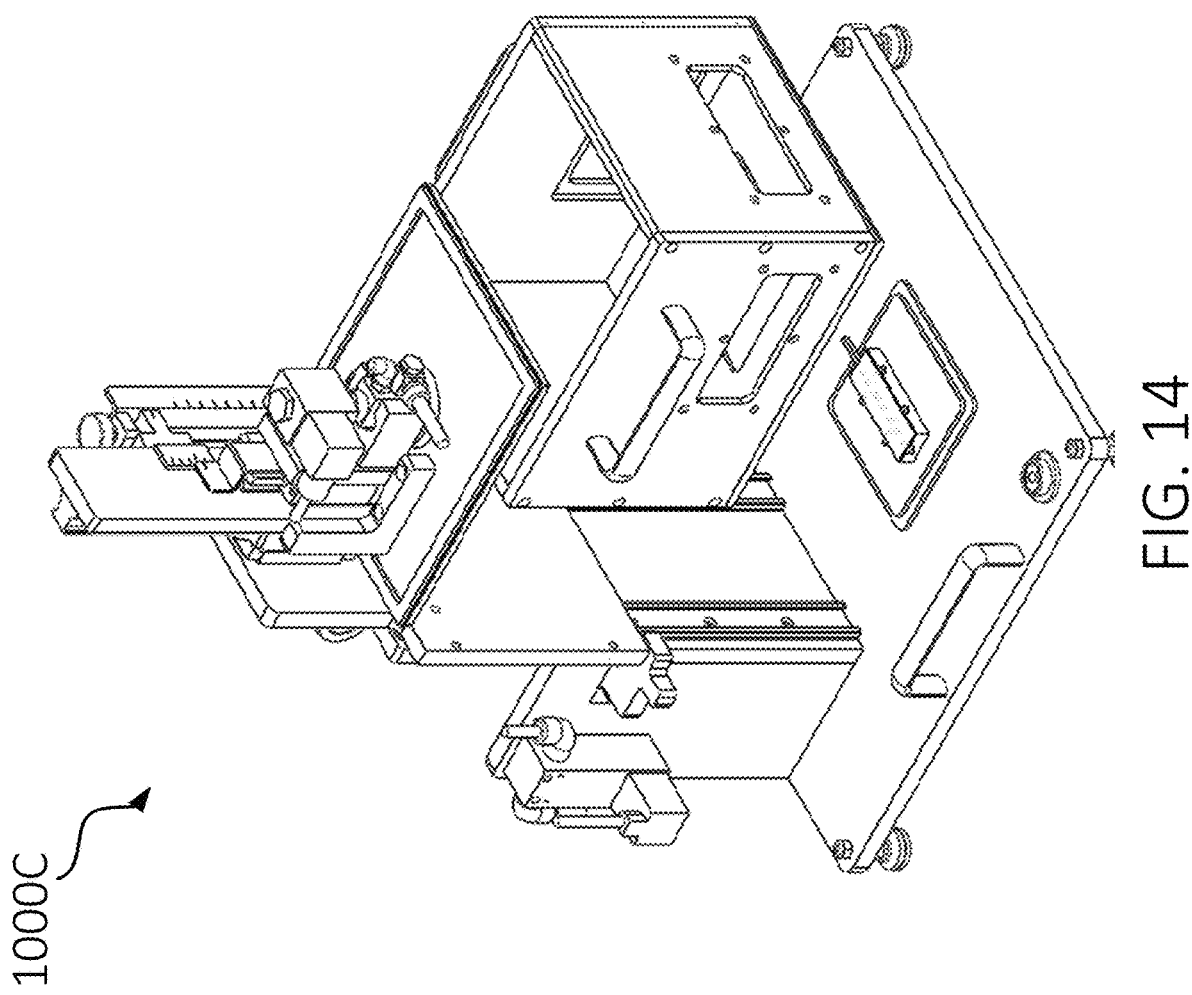

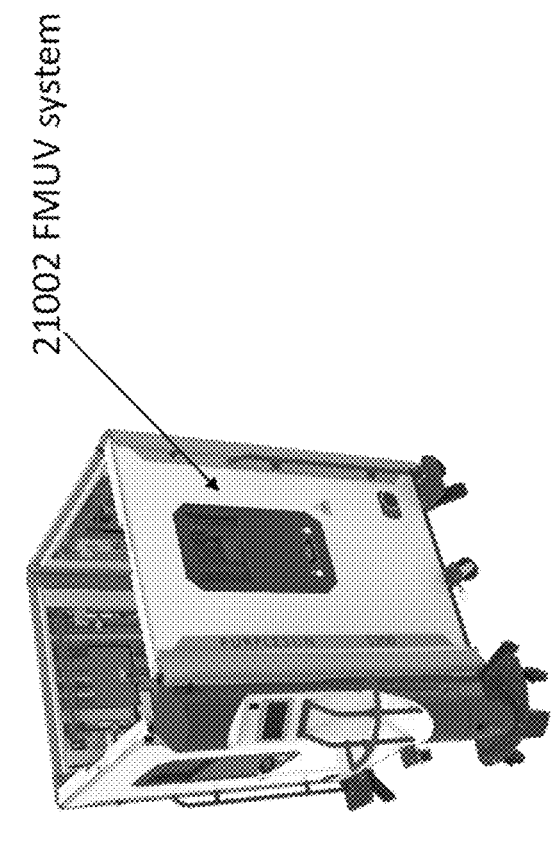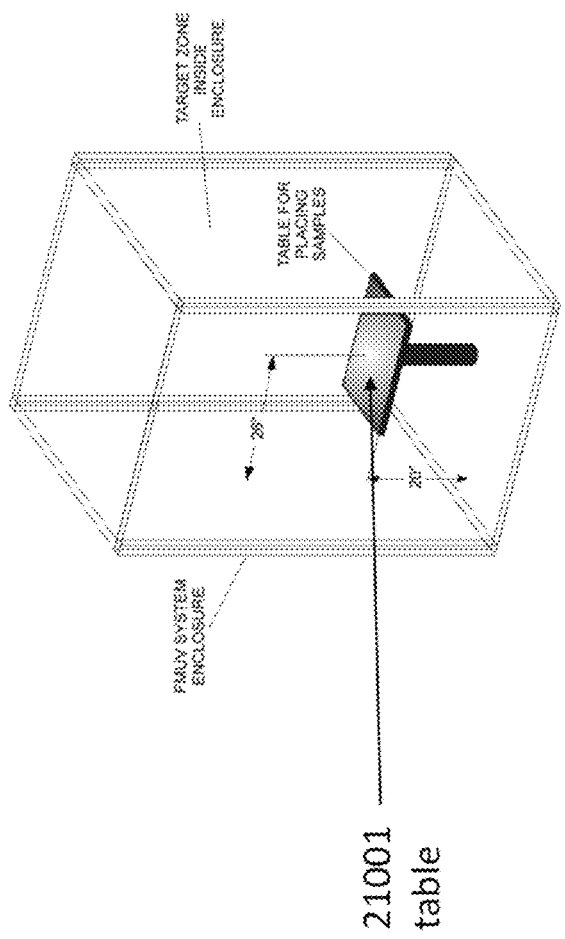
FIG. 21

Table 4: Control and Test Replicate CFU/Carrier Counts for *Staphylococcus aureus*

| Type | Replicate | CFU/Carrier | Average CFU/Carrier | Log10 Density | Mean Log10 Density |
|---|---|---|---|---|---|
| Control | 1 | 6.6E+05 | 1.7E+06 | 5.8 | 6.1 |
|  | 2 | 3.4E+06 |  | 6.5 |  |
|  | 3 | 9.3E+05 |  | 6.0 |  |
| Test | 1 | 3.6E+01 | 2.4E+01 | 1.6 | 1.3 |
|  | 2 | 2.7E+01 |  | 1.4 |  |
|  | 3 | 9.0E+00 |  | 1.0 |  |
| Range Log CFU Reduction |  |  |  |  | 4.8 – 5.1 |
| Range Average Percentage CFU Reduction |  |  |  |  | 99.9984% – 99.9992% |

*NOTE: No growth on carrier in Test 3.*

FIG. 25A

Table 5: Control and Test Replicate CFU/Carrier Counts for *Pseudomonas aeruginosa*

| Type | Replicate | CFU/Carrier | Average CFU/Carrier | Log10 Density | Mean Log10 Density |
|---|---|---|---|---|---|
| Control | 1 | 1.5E+06 | 1.9E+06 | 6.2 | 6.3 |
| | 2 | 1.7E+06 | | 6.2 | |
| | 3 | 2.4E+06 | | 6.4 | |
| Test | 1 | 9.0E+00 | 2.7E+01 | 1.0 | 1.2 |
| | 2 | 6.3E+01 | | 1.8 | |
| | 3 | 9.0E+00 | | 1.0 | |
| Range Mean Log CFU Reduction | | | | | 5.1 – 5.7 |
| Range Average Percentage CFU Reduction | | | | | 99.9992% – 99.9998% |

NOTE: *No growth on carrier in Test 1 & 3.*

FIG. 25B

AUTOMATED DEPOSITION OF MICROFILMS, SYSTEMS AND METHODS

RELATED APPLICATIONS

This patent application is a U.S. Continuation patent Application of PCT International Application No. PCT/US2020/056886, filed Oct. 22, 2022, which claims the benefit of and priority to U.S. Provisional Patent Application Ser. No. 62/924,313, filed on Oct. 22, 2019, each of which are hereby incorporated by reference herein in their entireties.

BACKGROUND

The present application generally relates to scientific instruments, devices and test methods, and more particularly relates to the testing of light-based technologies used for sanitizing and disinfection of surfaces for the purpose of controlling disease. Health care facilities often disinfect equipment and surfaces in operating rooms, patient rooms and other areas after patients are discharged to reduce the risk of infection to patients and health care workers. Benchmarking these disinfection devices and methods are hindered by our inability to reproducibly control microfilm deposition of an inoculant containing pathogens for the purpose of preparing testing samples.

SUMMARY

In one aspect, implementations include: a system configured to automatically deposit a variable film of an inoculant containing one or more pathogens, the system including: a base configured with a receptacle for a removable chamber; a liquid inlet receiver configured to provide the inoculant from a liquid inlet thereon to the removable chamber; a gas inlet configured to provide a pressurized gas from a gas tank to the removable chamber; and an adjustable nozzle configured to spray the inoculant from the liquid inlet and under the pressurized gas from the gas inlet.

Implementations may include one of more of the following features.

The base may include a control module configured to synchronize an opening of the liquid inlet and an opening of the gas inlet. The control module may be further configured to control an amount of the inoculant to be sprayed in the removable chamber. The control module may be further configured to control a pressure of the pressurized gas to be released that drive the inoculant from the liquid inlet to the removable chamber. The control module may be further configured to control a spray radius of the adjustable nozzle. The control module may be further configured to control a duration of spraying the inoculant from the adjustable nozzle. The control module may be further configured to control an angle of spraying the inoculant from the adjustable nozzle. The control module may be further configured to control a mixing ratio of the pressurized gas from the gas inlet and the inoculant from the liquid inlet.

The control module may be further configured to generate a set of control parameters based on a desired profile of the variable film to be deposited, and wherein the set of control parameters comprise at least one of: an amount of the inoculant to be sprayed, a pressure of the pressurized gas to be released, a spray radius, a spray duration, a spray angle, and a mixing ratio of the pressurized gas from the gas inlet and the inoculant from the liquid inlet.

The system may further include a removable chamber secured to the base. The removable chamber may be configured to enclose the adjustable nozzle. The removable chamber may be mechanically adjustable in at least one volumetric dimension. The at least one volumetric dimension may include one or more of: a height, a width, a length, or a radius. The system may further include: a controllable arm coupled to a top plate of the removable chamber, wherein the controllable arm is operable to adjust the at least one volumetric dimension of the removable chamber.

The removable chamber may be configured to receive one or more interchangeable stages holding at least one interchangeable insert for receiving the inoculant sprayed from the adjustable nozzle. The interchangeable insert may be capable of receiving a target surface on which the variable film is deposited. The one or more interchangeable stages may include a holding mechanism to hold the target surface. The removable chamber is sealed once connected to the base. The removable chamber may be configured to receive one or more interchangeable stages through a bottom plate of the removable chamber. The removable chamber may be configured to receive one or more interchangeable plates with at least one interchangeable insert through a bottom plate of the removable chamber. The removable chamber may include a protective layer configured to encapsulate the removable chamber such that sprayed inoculant is limited to the removable chamber.

In another aspect, implementations include a method that include: mounting a removable chamber on a base of a system for automatically depositing a variable film of an inoculant containing one or more pathogens; and controlling the deposition system to spray the inoculant from an adjustable nozzle of the system to a target surface located inside the removable chamber.

Implementations may include one or more of the following features.

Controlling the deposition system may include: synchronizing an opening of a liquid inlet that provides the inoculant and an opening of a gas inlet that provides a pressurized gas to drive the inoculant to the target surface. Controlling the deposition system may further include: controlling an amount of the inoculant to be sprayed to the target surface located inside the removable chamber. Controlling the depositing system further may include: controlling a pressure of the pressurized gas to be released from the gas inlet. Controlling the depositing system may further include: controlling a spray radius of the adjustable nozzle. Controlling the depositing system may further include: controlling a duration of spraying the inoculant from the adjustable nozzle. Controlling the depositing system may further include: controlling an angle of spraying the inoculant from the adjustable nozzle. Controlling the depositing system may further include: controlling a mixing ratio of the pressurized gas from the gas inlet and the inoculant from the liquid inlet.

Controlling the deposition system may include: generating a set of control parameters based on a desired profile of the variable film to be deposited, and wherein the set of control parameters comprise at least one of: an amount of the inoculant to be sprayed, a pressure of the pressurized gas to be released, a spray radius, a spray duration, a spray angle, a mixing ratio of the pressurized gas from the gas inlet and the inoculant from the liquid inlet, and a concentration of the one or more pathogens as deposited on the target surface.

Various implementations may be inherently low in cost compared to existing implantable neural modulation systems, and this may lead to wider adoption of neural modulation therapy for patients in need as well as reduction in overall cost to the healthcare system.

The details of one or more implementations are set forth in the accompanying drawings and the description below. Other features, objects, and advantages will be apparent from the description and drawings, and from the claims.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various configurations discussed in the present document.

FIG. 14 illustrates the separation of the volumetric chamber of an automated deposition device of FIG. 1, in accordance with at least one example of the present disclosure.

FIG. 21 illustrates an application for the automated deposition device for testing light-based disinfection technology, in accordance with at least one example of the present disclosure.

FIG. 25A illustrates lab testing results of an ultraviolet disinfection system validating using target surfaces treated with the automated deposition device and *Staphylococcus aureus*, in accordance with at least one example of the present disclosure.

FIG. 25B illustrates lab testing results of an ultraviolet disinfection system validating using target surfaces treated with the automated deposition device and *Pseudomonas aeruginosa*, in accordance with at least one example of the present disclosure.

DETAILED DESCRIPTION

The Automated Deposition System is an electrically operated spray deposition device that allows for the reproducible and homogeneous deposition of microorganisms, monolayers and or micro films onto target surfaces for the purposes of controlling concentration, density, pressure, volume, deposition angle, and spray radius with an interchangeable stage and interchangeable target surface for the study of micro depositions and microfilms of a variety of composites.

The present device is capable of spraying monolayers of microorganisms such as spores or bacterial cells, but is not limited to spraying live microorganisms and may be used to create monolayers of other microbes such as viruses and other organic or inorganic materials such as DNA, RNA molecules or other composites.

Figure 1:
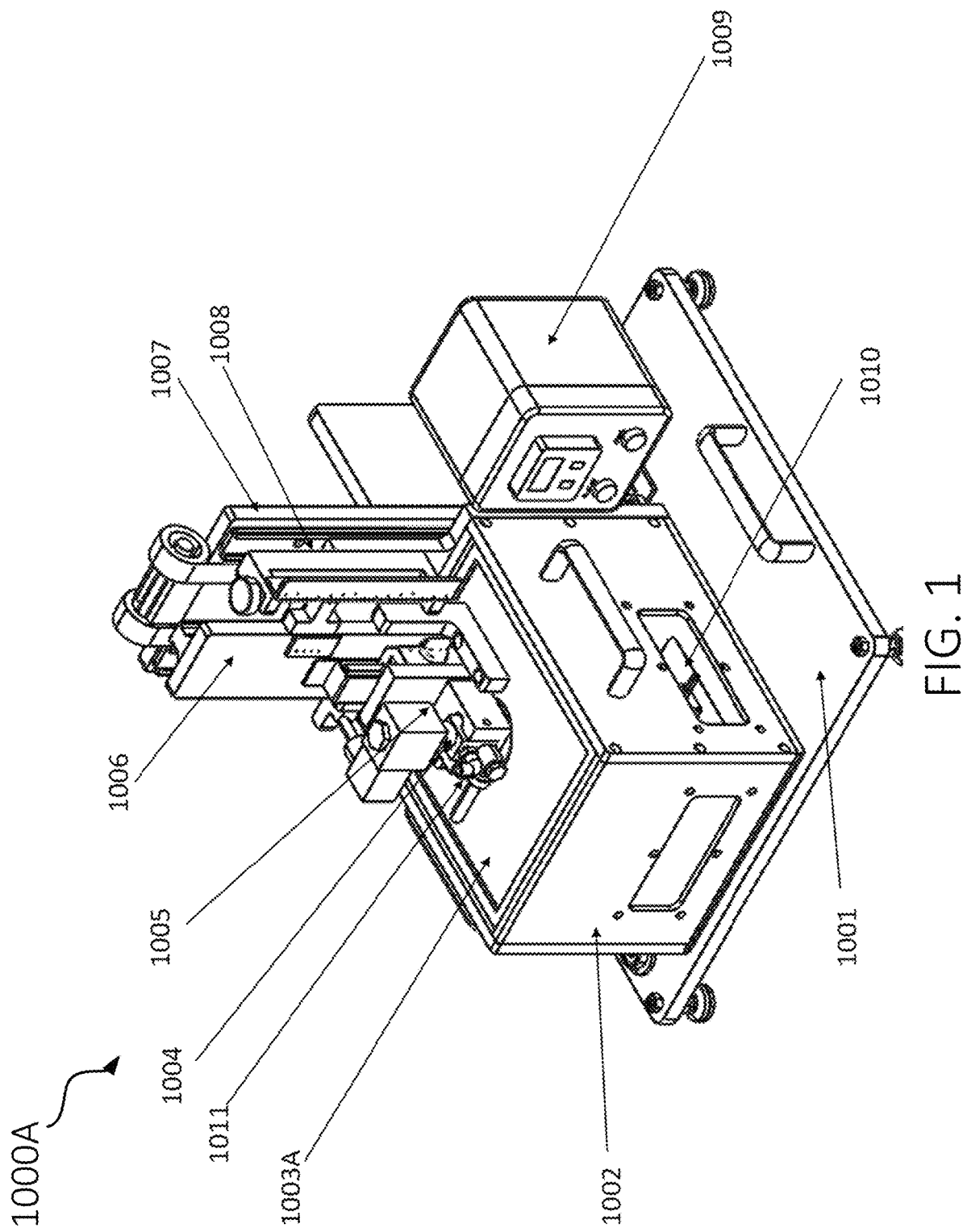
FIG. 1 illustrates a perspective view of an automated deposition device in a standard assembled and closed configuration, in accordance with at least one example of the present disclosure.

FIG. 1 illustrates a perspective view of one configuration of the Automated Deposition System. In the present configuration the device comprises a base structure 1001 in the form of a flat plate. Sitting on the base 1001 is an enclosed chamber 1002 which houses a stage 1010 which will hold the interchangeable surfaces onto which monolayers will be deposited. The chamber 1002 includes a removable and adjustable top plate 1003A that provides access to the internal stage holding the samples. Above the chamber 1002 is a nozzle 1004 used for spraying a solution inside the chamber onto a target surface. The nozzle 1004 is held in place by a nozzle holder 1005. The nozzle 1004 and the nozzle holder 1005 are attached to the arm 1006 which holds these components above the chamber 1002. The arm 1006 is affixed to tracks 1008 which are in turn attached to a mounting plate 1007 which enable the chamber assembly to be raised and lowered. The spray nozzle is operated by the controller 1009 which triggers the release of a spray in a precisely timed jet. As illustrated, the Automated Deposition System additionally includes a liquid inlet receiver 1011.

The Automated Deposition Device has connections for Nitrogen gas, oxygen gas, or other types of pressurized gas lines that are visible at the rear and towards the front. In this configuration nitrogen gas at approximately 29 psig can be delivered to the mechanical nozzle which sprays it into the chamber. Nitrogen gas or any other inert gas including air may be used as the propellant and the pressure that the propellant is regulated to is not limited to 29 psig but can span any reasonable pressure range from 0.0-100 psig or more.

The windows of the chamber can facilitate observation of the deposition process inside the chamber. With appropriate lighting the conical spray is briefly visible, and the deposition may appear as a wet sheen on the surface of the carriers before rapidly evaporating.

In one configuration, the chamber 1002 can be raised up for ease of access to the target surface. This facilitates safe removal and placement of samples while still maintaining a tight seal when the chamber is lowered and closed for spraying. In this configuration a track and gear mechanism is employed but other mechanisms that raise and lower objects can suitably be applicable without impinging on the integrity of the seal at the base of the chamber. Other mechanical mechanisms such as screws threads may also be employed and electromechanical mechanisms including the use of solenoids would also make for suitable and safe operation provided they created an adequate seal around the base or other areas minimize leakage of aerosols that might escape during the testing process. This provides an extra level of security since this device is intended to be placed inside a Biosafety hood or a chamber which is not represented can be implemented so the need of a biosafety hood is not necessary.

The nozzle in this device has an adjustable spray radius which can be adjusted according to the size of a sample in this case a glass slide. To fit a spray radius within a particular dimension, for example the specific width of the glass slide, both the spray nozzle and the distance to the glass slides can be adjusted to obtain an improved coverage. These configurations can also contribute to making fine adjustments in the amount of organism sprayed on the target surface. The concentration of a particular microbe can be controlled through calculations and adjustments to the parameters of some implementations described in the present disclosure.

The removal of the chamber from the base can facilitate handling of samples and disinfection of the components of the Automated Deposition System. The Automated Deposition System can be cleaned and sanitized before and after use for testing. A variety of methods and agents can be used to clean, disinfect, and sterilize the test apparatus, including autoclaving, ultraviolet disinfection, hydrogen peroxide vapor disinfection and wiping with disinfectant wipes.

The device can use typical glass slides for deposition or any other interchangeable target surface of interest. In the present configuration, the dimensions are 1"×3". Dimensions of desired target surfaces may be 1"×2", 1"×3", 2"×2", 3"×2", 3"×5", 7"×5", or any other footprint that fits within the chamber 1002. The cone angle and spray area can be adjusted by the volumetric chamber and by adjusting the height or positioning in relation to the target surface. Wider or narrower spray radii are possible. Raising the height of the nozzle and adjusting the nozzle spray radius can be adjusted to suit the dimensions of the target surface being inoculated.

Scanning Electron Microscopy (SEM) was used to study the deposition of bacteria that were sprayed with implementations of the automated deposition system. Viewing different areas within the spray radius allowed for the study of the homogeneity or evenness of deposition of the monolayer bacterial cells. The images captured were used to search for any evidence of clustering of cells. The *S. aureus* cells are about 1-2 microns in diameter and appear whitish. All of the cells visible are lying on the glass surface which remains as the dark background and appears relatively flawless and without asperities at this magnification. Staphylococci have a natural tendency to cluster together but although some cells in this image are lying next to other cells they are still lying in a monolayer.

A high degree of regularity in the monolayer or evenness of deposition can result in a high degree of accuracy in any data collection utilizing these samples. The reason is that if one in a thousand cells were shadowed and protected from ultraviolet exposure by being clustered, then one thousandth of the population will behave as if they are resistant to the exposed ultraviolet dose. That would represent a disinfection rate of 99.9% and may well place limits on the accuracy of tests which are seeking to understand the rate constants for microorganism inactivation in order to measure kill rate reductions of 99.9999% or greater. Because the degree of clustering may not be known with absolute accuracy, it may assist with testing to deposit the desired microfilm comprised of the microorganisms of interest in a homogeneous monolayer in high enough concentrations that kill rates or disinfection rates of 99.9999% can be measured.

The Automated Deposition System can be configured to deposit pathogens, such as *Staphylococcus aureus* and *Pseudomonas aeruginosa* cells, in monolayers. Achieving high density monolayers of viable bacteria cells can assist in demonstrating high reduction rates in terms of Colony Forming Units (CFU) or other means of measuring microorganism quantification when ultraviolet light systems are used for testing.

In configurations of the present subject matter, devices, systems, and methods related to automated deposition of a liquid, organism, and deposition on glass slides, steel discs or otherwise. Specific configurations of the disclosed device, delivery system, and method will now be described with reference to the drawings. Nothing in this detailed description is intended to imply that a particular component, feature, or step is essential to the implementations disclosed in the present disclosure.

This above discussion is intended to provide an overview of subject matter of the present disclosure. It is not intended to provide an exclusive or exhaustive explanation of all likely implementations that flow from the disclosed implementations. The detailed description is included below to provide further information.

FIG. 1 illustrates a perspective view of a configuration of an automated deposition device 1000A in a standard assembled and closed configuration. In this configuration, the device comprises a base structure 1001 in the form of a square plate. In this and other configurations, the base structure may have a plurality of shapes (e.g., circular, rectangular, hexagonal, triangular, or irregular) in combination with a plurality of varying footprints throughout the base structure. In this and other configurations, the base of the base structure is configured to rest on a plurality of varying surfaces (e.g., floor, benchtop, table, or raised, or other horizontal surface) and provide a stable frame for the device. In this and other configurations, a plurality of casters, collapsible stand, or other interchangeable platform may be disposed on the bottom of the base structure. In this and other configurations, one or more chambers and stages of varying types can be disposed on the base structure that are controlled via a controller to create volumetric changes, pressure changes, cone angle changes, and concentration of deposit control.

FIG. 1 further depicts a chamber, 1002, is operably coupled to the base structure 1001. In the present configuration, the device comprises the chamber 1002 in the form of a rectangular box. In this and other configurations, the chamber may have a plurality of shapes and sizes (e.g., cylindrical, cubic, hexagonal, triangular, spherical, or irregular) in combination with a plurality of varying footprints throughout the base structure, and furthermore in combination with varying volumes which can be adjustable for the purposes of testing. Nonlimiting examples of configurable volumes include 100 in$^3$, 151 in$^3$, 200 in$^3$, 250 in$^3$, 270 in$^3$, 300 in$^3$, 350 in$^3$, 363 in$^3$, 389 in$^3$, 400 in$^3$, or any other desired volume that may fit upon the base. In this and other configurations, the device possesses one or more chambers. Non-limiting examples include one chamber, two chambers, three chambers, four chambers, five chambers, six chambers, seven chambers, eight chambers, nine chambers, ten chambers, eleven chambers, twelve chambers, or more in accordance with the total desired quantity to create an assembly line system for larger scale automated depositions. Additionally, the one chamber 1002 in FIG. 1 is vertically aligned directly centered atop the base structure 1001. In this and other configurations, the one or more chambers are operably coupled to the base structure at a variety of positions. Non-limiting examples include the chamber to be aligned above, underneath, or offset adjacent with respect to the base. In FIG. 1, the chamber 1002, is positioned level atop the base structure. In this and other configurations, the one or more chambers may be positioned on the same level on the base structure, different level on the base structure, separate from the base structure, or a combination thereof. Moreover, the chamber 1002 in FIG. 1 is enclosed around one stage 1010. In the present configuration, the chamber 1002, encapsulates one rectangular-shaped stage 1010, positioned atop the base structure 1001. In this and other configurations, the stage may have a plurality of shapes (e.g., cylindrical, cubic, hexagonal, triangular, spherical, or irregular) in combination with a plurality of varying footprints throughout the base structure. In this or other configurations, a chamber or base may possess one or more stages as shown as 1010. Non-limiting examples include one stage, two stages, three stages, four stages, five stages, six stages, seven stages, eight stages, nine stages, ten stages, eleven stages, twelve stages, or more.

In this or other configurations, one or more stages, or one or more nozzles may be configured to translate. In this or other configurations, the chambers, stages, and nozzles are modular. In this or other configurations, additional chambers and stages may be added onto or taken away to provide additional configurations and extend or decrease the number of items receiving deposition. Again, in this or other configurations, additional nozzles may be added or taken away to provide varied deposition configurations depending on the set-up of the target surface or item receiving deposition. Additionally, the same nozzle may be capable of translating to additional chambers to provide additional deposition configurations depending on the quantity of chambers, stages, target surfaces or items receiving deposition.

Figure 2:
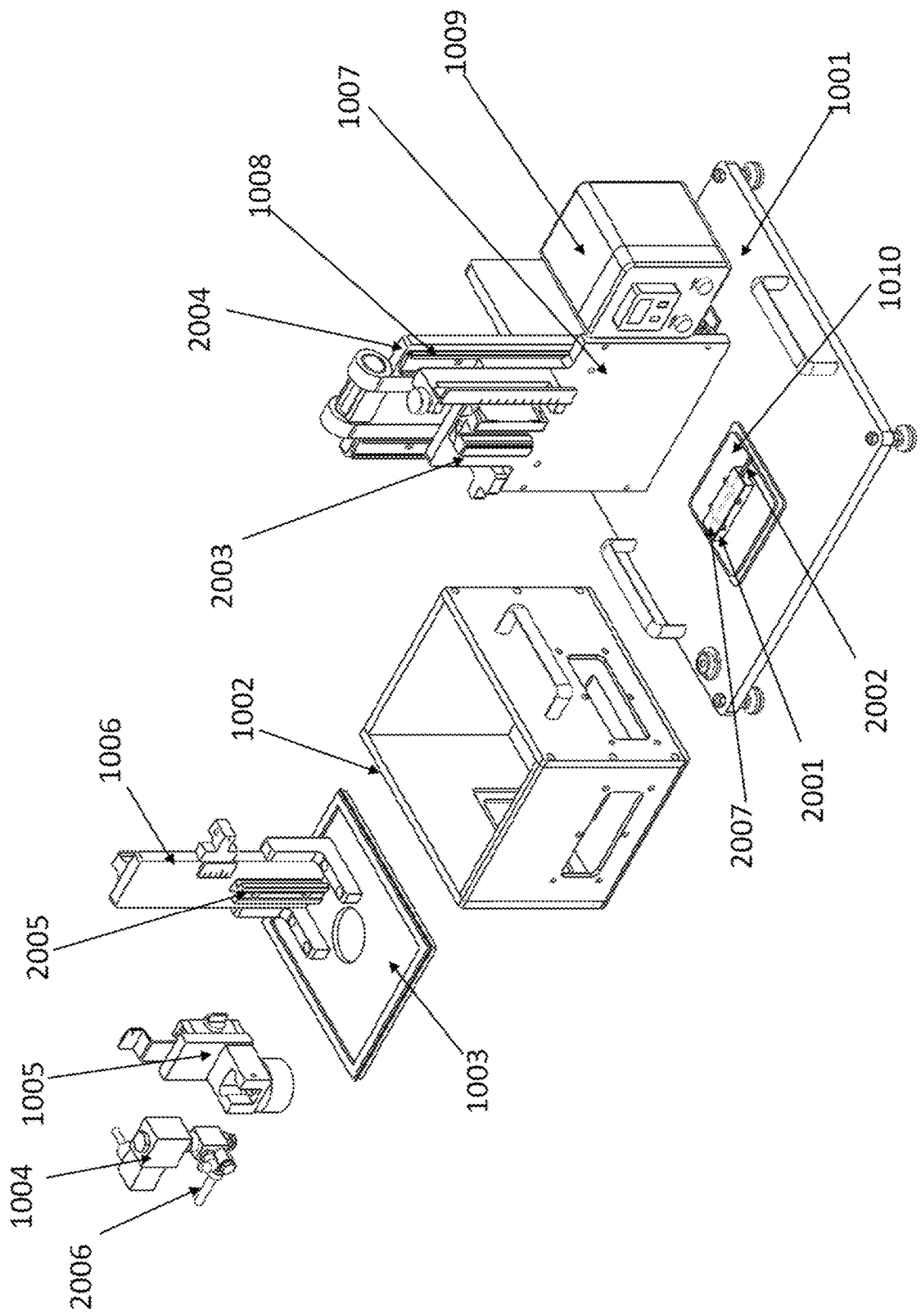
FIG. 2 illustrates an exploded view of the overhead view of the automated deposition device of FIG. 1, in accordance with at least one example of the present disclosure.

FIG. 2 illustrates an exploded view of the overhead view of the automated deposition device of FIG. 1. The present configuration is comprised of seven components for the purpose of this representation. The components are the nozzle assembly, holder 1005, arm 1006, top plate 1003, volumetric chamber 1002, interchangeable stage assembly, and base unit. In the present configuration, the base unit is notably comprised of the base 1001, mounting plate 1007 with two tracks 1008, back plate 2004, rail 2003, and controller 1009, among other components. Within the present configuration, the interchangeable stage subassembly, is notably comprised of an interchangeable stage 1010 holding an interchangeable stage insert 2001 and target surface mechanism 2002. Additionally, the arm subassembly is notably comprised of an arm, with an attached guide 2005. Furthermore, in the present configuration, the nozzle subassembly is notably comprised of a nozzle 1004 with a gas inlet 2006. In this configuration, there exists a three-tiered system of configurable height to achieve variable heights and volumetric enclosures of device components to control the aerodynamics of the deposition process. The tracks, 1008, are operably coupled to the mounting plate, 1007, and mechanically fixed to the back plate 2004 to facilitate vertical translation of the mounting plate and therefore providing an adjustable volume by way of a change in the vertical direction and horizontal plane. The arm is operably coupled to the rail and is also mechanically fixed to the top plate, 1003 in other configuration the arm and the top plate may be separated. Additionally, the arm is mechanically fixed to a guide, 2005, which is operably coupled to the exchangeable holder, 1005. The holder is mechanically fixed to the nozzle, 1004, the holder allows for different types, sizes, shapes, and types of nozzles to be utilized. Furthermore, in this and other configurations, the nozzle is comprised of a gas inlet 2006 to facilitate pressurized propellant of a deposition solution. In this and other configurations, the gas inlet may accept a variety of propellant gasses. Non-limiting examples include compressed air, steam, nitrogen, or any other inert gas. In this configuration, due to the operable coupling of the aforementioned components, the vertical translation employed by the track and mounting plate interface introduces a configurable height for the chamber, nozzle, and top plate with respect to the base unit.

In this configuration, this height variability allows for necessary access to the target item receiving deposition. The height is variable at, for example, 1 inch, 2 inches, 3 inches, 4 inches, 5 inches, 6 inches, 7 inches, 8 inches, 9 inches, 10 inches or higher. The vertical translation employed by the rail and arm interface introduces a configurable height for the top plate and nozzle with respect to the chamber. Therefore, the overall volume of the chamber is deemed configurable by way of adjusting the height of the internal top surface of the chamber. The vertical translation employed by the guide and holder interface introduces a configurable height for the nozzle with respect to the top plate. All aforementioned components within this and other configurations are intended to be removable and interchangeable from the system. This allows for deposition of various liquids via the nozzle at various heights from target surfaces, within different volumetric chambers.

Figure 3:
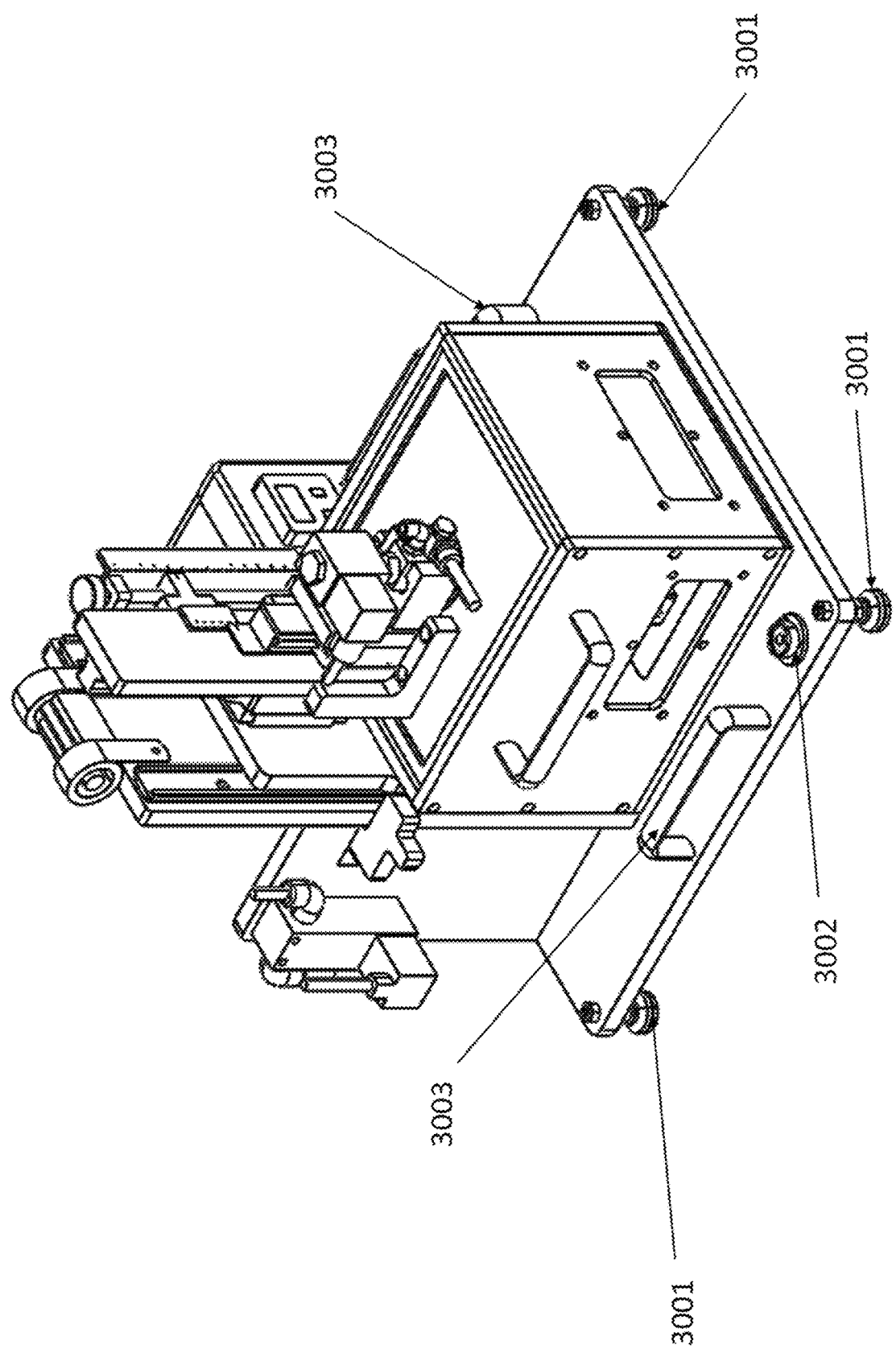
FIG. 3 illustrates a left perspective view of the automated deposition device of FIG. 1, in accordance with at least one example of the present disclosure.

FIG. 3 illustrates a perspective view of the automated deposition device of FIG. 1. FIG. 3 depicts the automated deposition device that includes a base 1001 containing four adjustable height legs, 3001, to facilitate leveling of the device with respect to ground and to adapt to various surfaces or platforms the device may sit upon. In this or other configurations, a leveling assist mechanism 3002, may be present on the base 1001 to facilitate in adjusting the levelness of the device. In this or other configurations, the device may or may not include casters attached to the support legs of the base 1001 to facilitate transport of the system. In this or other configurations, the base may possess permanent or interchangeable support legs. Non-limiting examples include one leg, two legs, three legs, four legs, five legs, six legs, seven legs, eight legs, nine legs, ten legs, eleven legs, or twelve legs. In this or other configurations, the device may include one or more handles, 3003, to assist in transport of the device between desired work areas. Non-limiting examples include one handle, two handles, three handles, four handles, five handles, six handles, seven handles, or eight handles, or different types of mechanisms for transportability of the system. In this or other configurations, the device may include one or more tracks, 1008, running vertically along centerline of the mounting plate 1007, which may be configured to attach to the one or more arms, 1006, to allow the one or more arms to translate the chamber, holder, nozzle, and top plate vertically within the structure. In this or other configurations, the one or more nozzles may further comprise a pivot axis on the end that operably couples to the base or arm structure, wherein the pivot axis is configured to allow the nozzle to be adjusted at a variety of angles relative to the base structure. Non-limiting examples include nozzles arranged vertically, horizontally, or any angle in-between horizontal and vertical. A nozzle mounted on a pivot axis may allow for a uniform spray of a monolayer film to be deposited on irregular surfaces or surfaces that may not have the ability to be mounted parallel to the base 1001.

Figure 4:
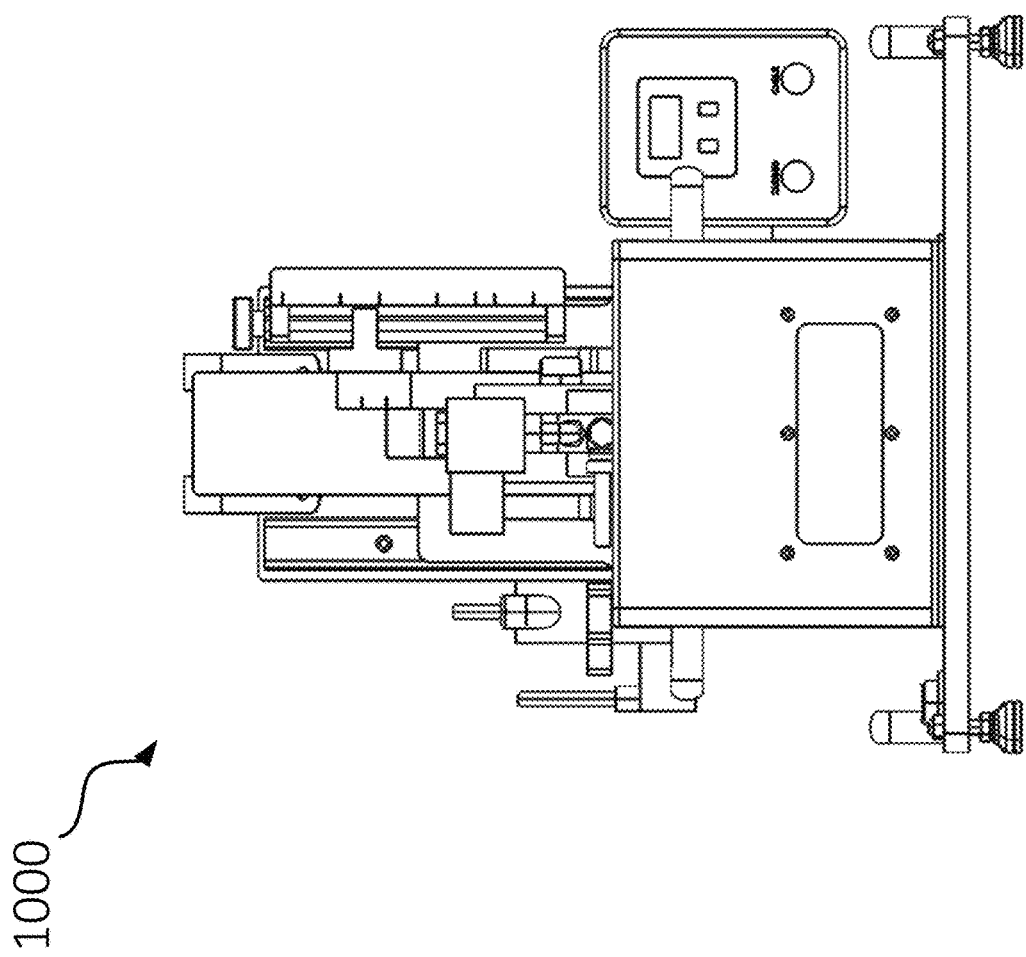
FIG. 4 illustrates a front view of the automated deposition device of FIG. 1, in accordance with at least one example of the present disclosure.
Figure 5:
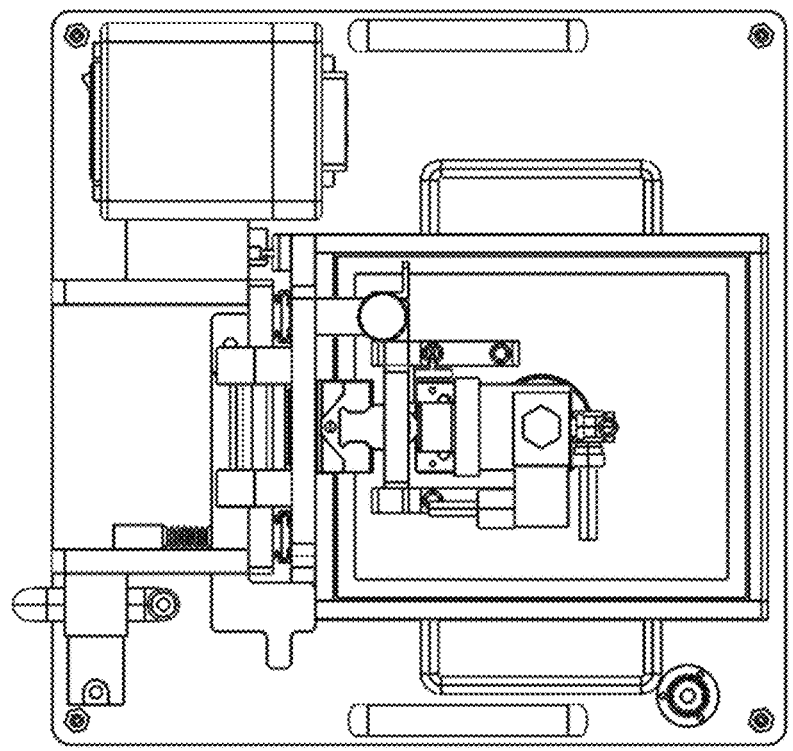
FIG. 5 illustrates a top view of the automated deposition device of FIG. 1, in accordance with at least one example of the present disclosure.
Figure 6:
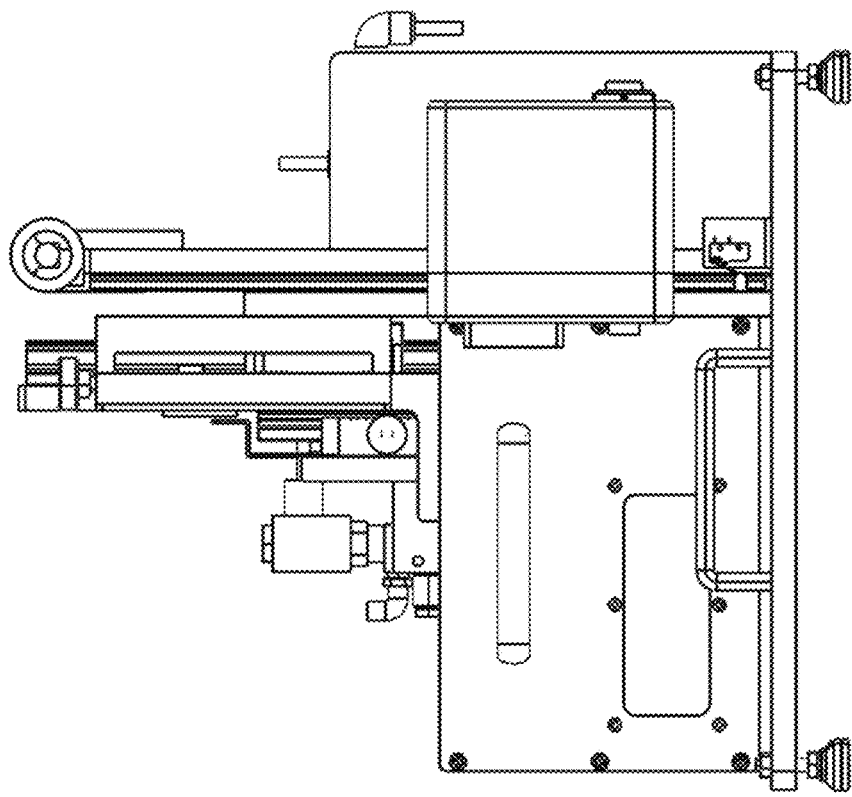
FIG. 6 illustrates a right-side view of the automated deposition device of FIG. 1, in accordance with at least one example of the present disclosure.
Figure 7:
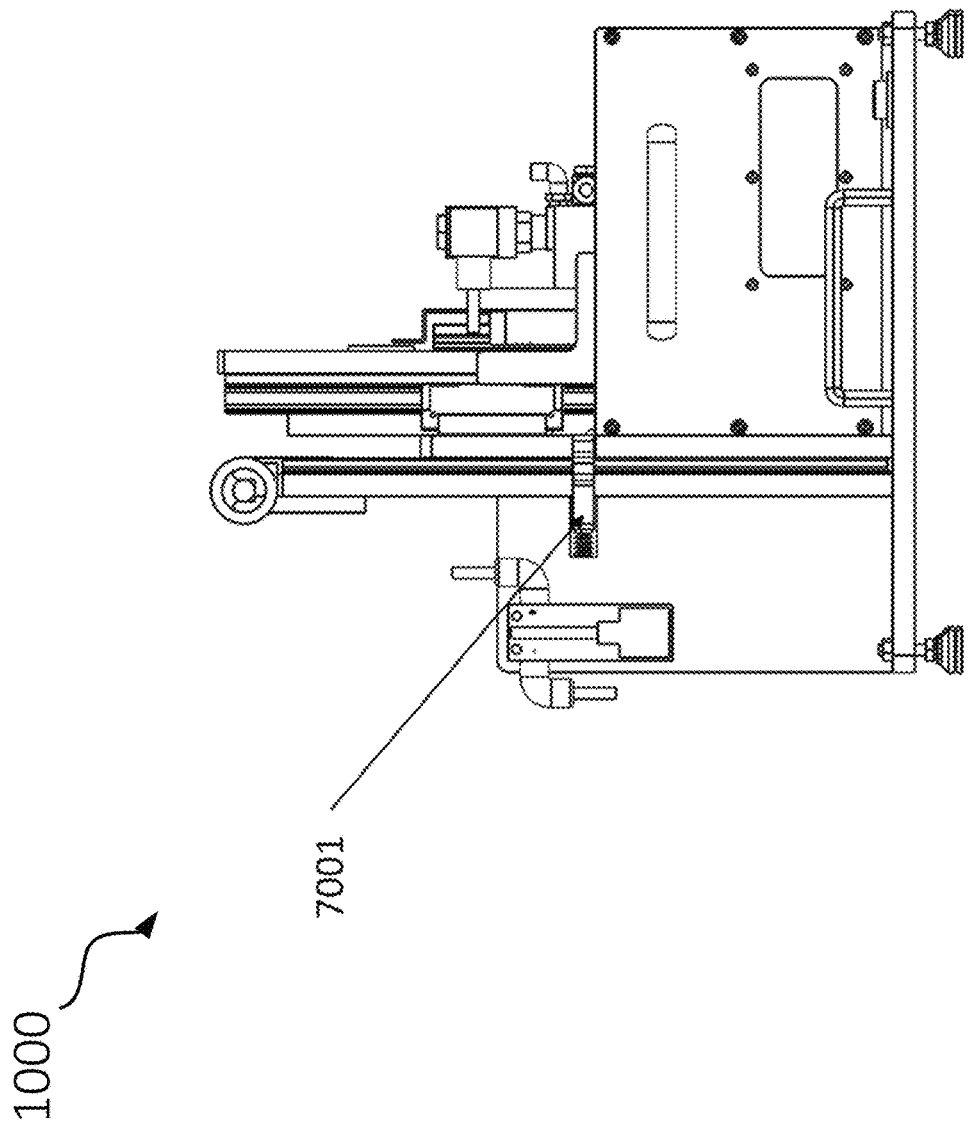
FIG. 7 illustrates a left side view of the automated deposition device of FIG. 1, in accordance with at least one example of the present disclosure.

FIG. 4 illustrates a front view of the automated deposition device of FIG. 1 assembled and closed configuration (labelled 1000). FIG. 4 illustrates one nozzle, 1004, above the chamber 1002, which may be mechanically fixed to a holder 1005. In this or other configurations, the nozzle and holder may be operably coupled to an arm, 1006, by way of a guide, 2005. Furthermore, in this or other configurations, one or more arms may be operably coupled to a top plate, 1003. In this or other embodiments, the arm may be mechanically operated to translate vertically such as to control the height of the top plate with respect to the chamber and thus the chamber volume. Additionally, the holder and nozzle may be mechanically operated to translate vertically such as to control the height of the nozzle with respect to the top plate. In this and other embodiments, the volume of the chamber as well as the height of the nozzle with respect to the top of the chamber may be configured by way of a variety of methods. Non-limiting examples for volumetric adjustment include chambers with an adjustable threaded top, customizable sized chambers, and expandable and contractable chamber walls in all directions. Non-limiting examples for nozzle height adjustment include gear racks, worm gear adjustment, linear rail adjustment, pulley-driven adjustment, fixed mounting points for fastening, and hinged arms. In this or other configurations, the device possesses a controller that can provide an operator with the ability to electrically configure the aforementioned parameters. This controller may additionally provide device feedback for adjusting the height and volumetric parameters. Non-limiting feedback and control items include device status, cycle count, height and volume relationships, safety warnings, target surface type, organisms for deposition, and component locations. Furthermore, the controller may configure the duration and frequency of programmed multiple spray operations for the purpose of controlling total deposition quantity. Nonlimiting examples of both spray durations and frequencies of spray include 0.05 s, 0.1 s, 0.2 s, 0.3 s, 0.55 s, 0.75 s, 1 s, 2 s, and 10 s. While a longer spray duration can deposit more organism onto the target surface, the spray rate can also be adjusted to facilitate rapid inoculation of multiple target surfaces in an automatic manner.

FIG. 5 illustrates a top view of the automated deposition device of FIG. 1 in an assembled configuration and shows the base, 1001, with the configurable volume chamber, 1002, with top plate 1003, and the nozzle, 1004, with holder, 1005, vertically aligned with respect to each other atop the base. In this and other configurations, the chamber, stage, nozzle, and holder may be aligned such that the deposition operation is centered on the target surface or item.

FIG. 6 illustrates a right side view of the automated deposition device of FIG. 1 in an assembled and closed configuration. In this and other configurations, nozzle and stage may be aligned and fixed such that deposition operation is directed purely perpendicular to the target surface or item receiving deposition.

FIG. 7 illustrates a left side view of the automated deposition device of FIG. 1, in an assembled and closed configuration. In this or other configurations, the chamber 1002 may be mechanically locked in a closed configuration to ensure the chamber does not inadvertently translate away from the stage during operation. The chamber lock, 7001, present in this configuration may be operably coupled to the back plate. The manipulation of this chamber lock with respect to the configured height of the mounting plate, 1007, introduces the ability to affix the chamber flush to the base, 1001, during deposition operation or suspended above the base to provide accessibility for manipulation of the target item, insert, and stage.

FIG. 8 illustrates the chamber which is to be utilized with the automated deposition device of FIG. 1. In the present configuration, the chamber comprises three transparent surfaces, 8001, present to facilitate a proper field of view for an operator. In this and other configurations, the chamber possesses a plurality of transparent surfaces for viewing through chamber surfaces. Non-limiting examples include one surface, two surfaces, three surfaces, four surfaces, five surfaces, six surfaces, or all surfaces. In the present configuration, the chamber comprises two handles, 8002, for assistance in movement of the chamber. In this and other configurations, the chamber handles may be operably coupled to the chamber at a variety of positions. Non-limiting examples include on the front of the chamber, the sides of the chamber, the top of the chamber, behind the chamber, underneath the chamber. In the present configuration, the chamber possesses an access point to the stage, 8003, on the bottom side of the chamber. In this and other configurations, the chamber may possess access points to facilitate manipulation of the target item receiving deposition in a variety of positions. Non-limiting examples include access from the front of the chamber, access from either side of the chamber, access from the top of the chamber, access by way of moving the stage, or access by way of moving the chamber. In this and other configurations, the access area for manipulating the target item receiving deposition may have a plurality of shapes (e.g., cylindrical, cubic, hexagonal, triangular, spherical, or irregular) dependent on the shape of the stage, 1010. Non-limiting examples of chamber access points include doorways, cutouts, trays, and moving platforms.

Figure 8:
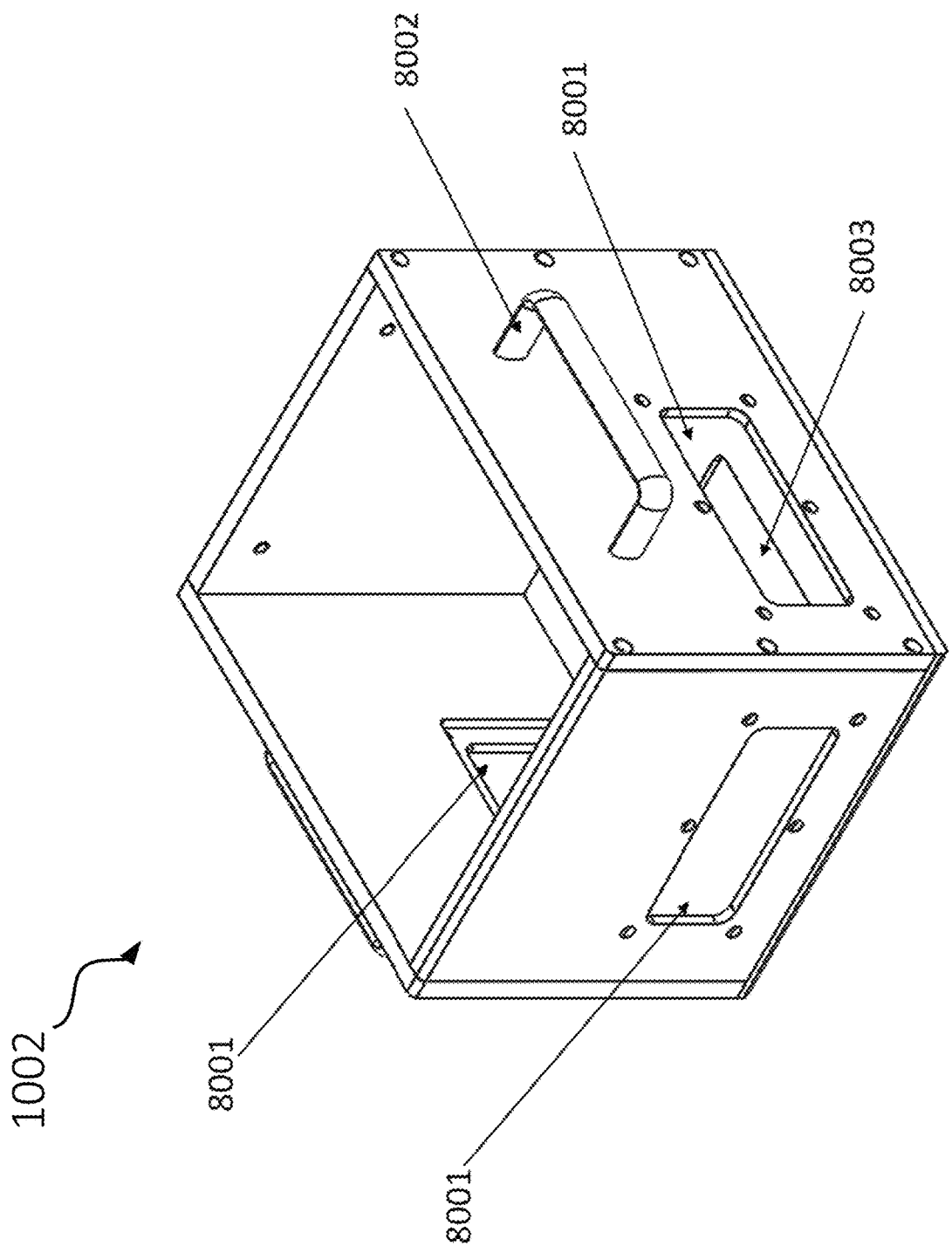
FIG. 8 illustrates the volumetric chamber which is to be utilized with the automated deposition device of FIG. 1, in accordance with at least one example of the present disclosure.
Figure 9:
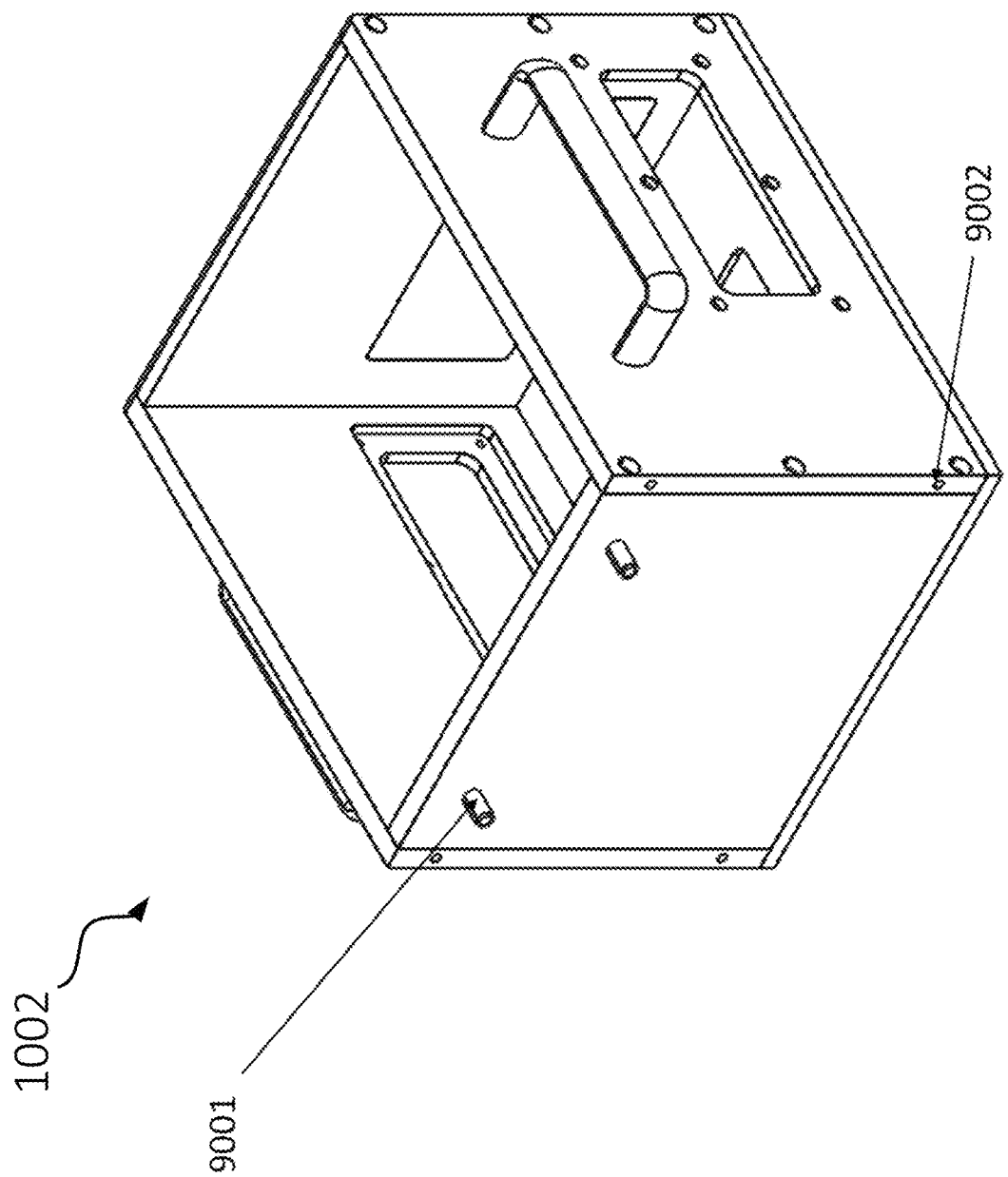
FIG. 9 illustrates a perspective rear view of the volumetric chamber of FIG. 8, in accordance with at least one example of the present disclosure.

FIG. 9 illustrates a perspective rear view of the chamber of FIG. 8. In the present embodiment, the chamber comprises two pin alignment features 9001. In this and other configurations, the chamber may possess a variety of mechanical alignment features used to facilitate positioning of the chamber 1002 with respect to the arm 1006. Non-limiting examples include one alignment feature, two alignment features, three alignment features, four alignment features, five alignment features. Additionally, in this and other configurations, fastening features, 9002, may be present to fix the chamber 1002 to the arm to maintain a fixed relationship during any expected motion. In this and other configurations, the chamber may be fastened to the mounting plate by way of a variety of fastening features. Nonlimiting examples include clamps, screws, pins, and hooks.

Figure 10A:
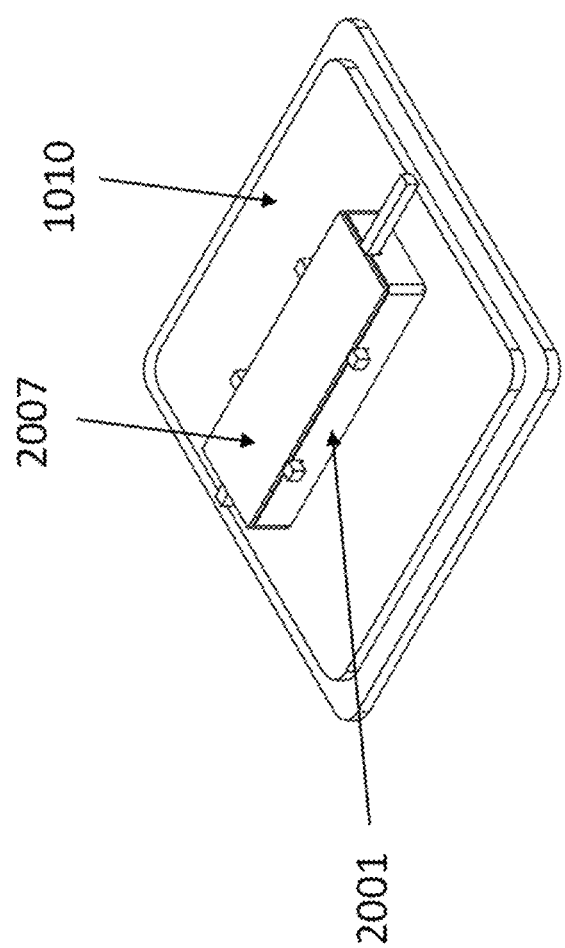
FIGS. 10A-10C illustrate a removable stage, removable insert, and removable target surface mechanism of the automated deposition device of FIG. 4, in accordance with at least one example of the present disclosure.
Figure 10B:
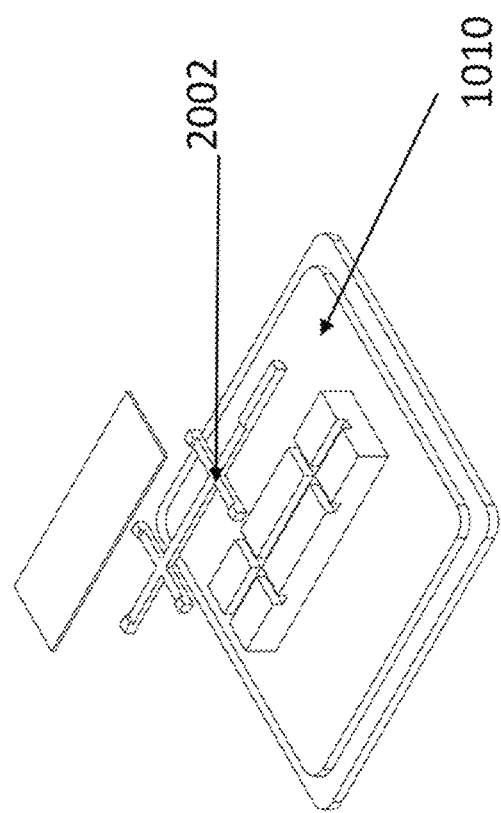
Figure 10C:
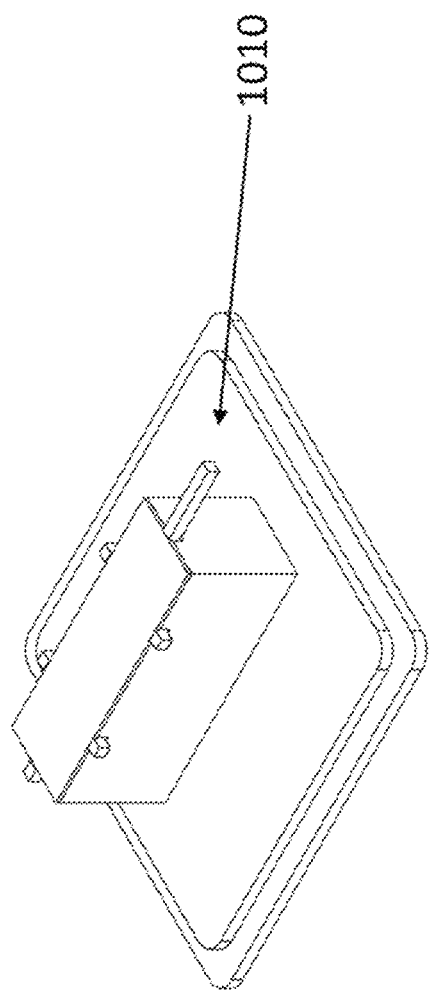

FIGS. 10A-10C illustrate a stage 1010, stage insert 2001, target surface 2007, and extraction mechanism 2002 of the automated deposition device of FIG. 4. Within the confines of the present disclosure, extraction mechanism and removable target surface mechanism can be used interchangeably. In this and other configurations, the stage is mechanically positioned on the base, 1001, in a repeatable manner. Dependent upon application and target surface receiving deposition, this stage is comprised of configurable geometry along with the stage insert. In this and other configurations, the height of the surface shall be interchangeable as determined by customizability of the stage. In this and other configurations, the height of the insert may be configured through a variety of ways such that the stage insert shown in FIG. 10B is of a shorter profile in comparison to the stage insert depicted in FIG. 10C. Non-limiting examples include stackable stage items, variable height stages, a configurable height platform, or suspended-height inserts. In this and other configurations, the device possesses an extraction mechanism 2002. This item is intended to serve as an extraction mechanism for removing the target surface 2007 from the stage insert 2001. Present in this configuration, the extraction mechanism sits beneath the stage insert and is comprised of a feature that allows for operator manipulation for purposes of removing the target surface from the entire deposition device. In this and other configurations, the device may possess a variety of mechanisms for controlled alignment and controlled extraction of the stage insert or target surface from the stage. Non-limiting examples include keyed cage nests, alignment pins, raised-height platforms, lever-controlled platforms, or alignment pads.

Figure 11:
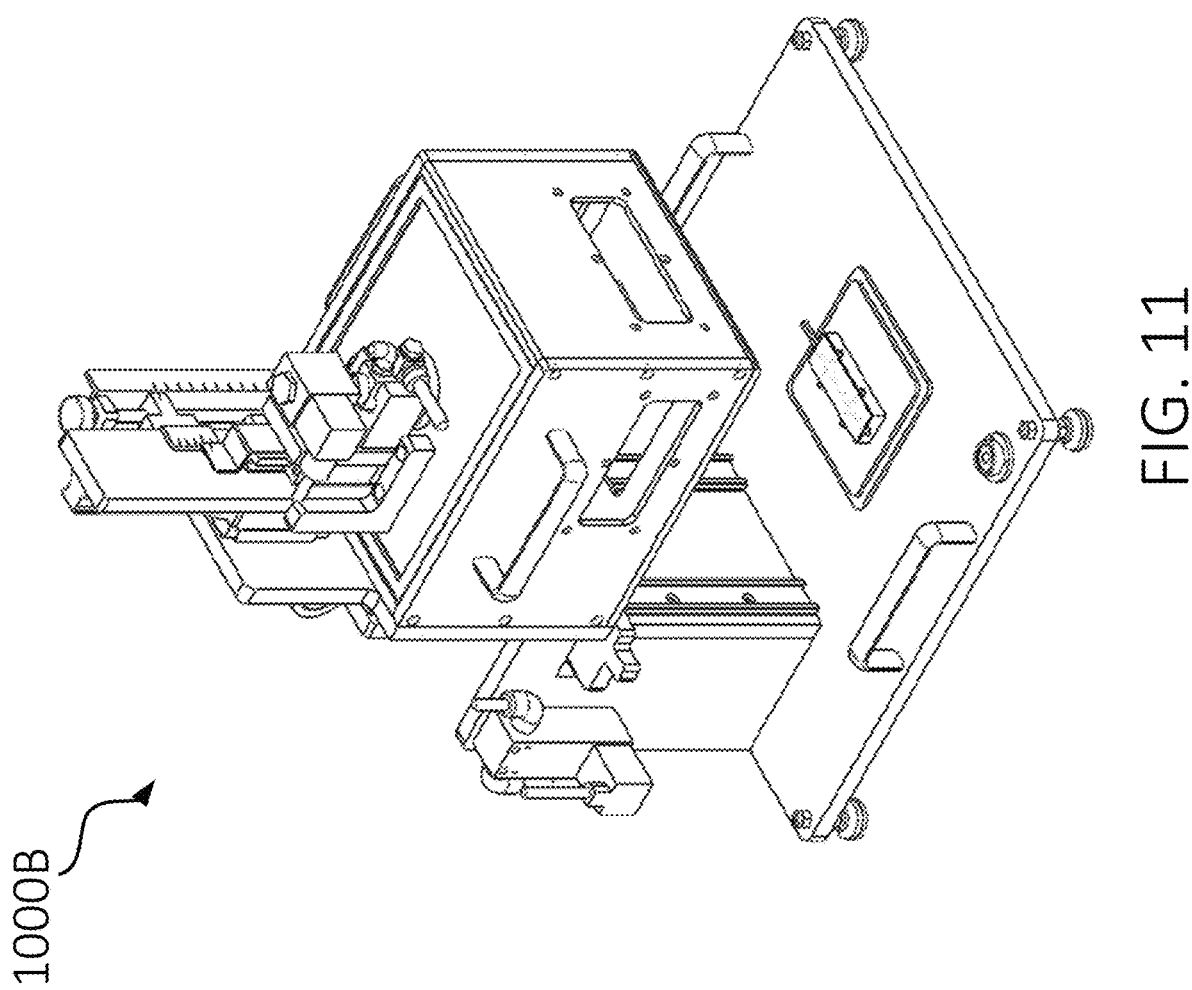
FIG. 11 illustrates the adjustable volumetric chamber in the up position of the automated deposition device of FIG. 1, in accordance with at least one example of the present disclosure.

FIG. 11 illustrates the adjustable chamber height of the automated deposition device of FIG. 1. In the present configuration (labelled 1000B), the chamber 1002, nozzle 1004, top plate 1003, holder 1005, guide 2005, arm 1006, rail 2003, and mounting plate 1007 all translate vertically upward via the tracks 1008 and may be temporarily fixed in an up locked position by way of the chamber lock 7001. This height adjustment of the aforementioned components allows for operator accessibility to the stage 1010, stage insert 2001 and extraction mechanism 2002. This access introduces the ability for an operator to safely manipulate, remove, or add the stage insert 2001 or target surface 2007 that has received or will receive material or liquid deposition.

Figure 12:
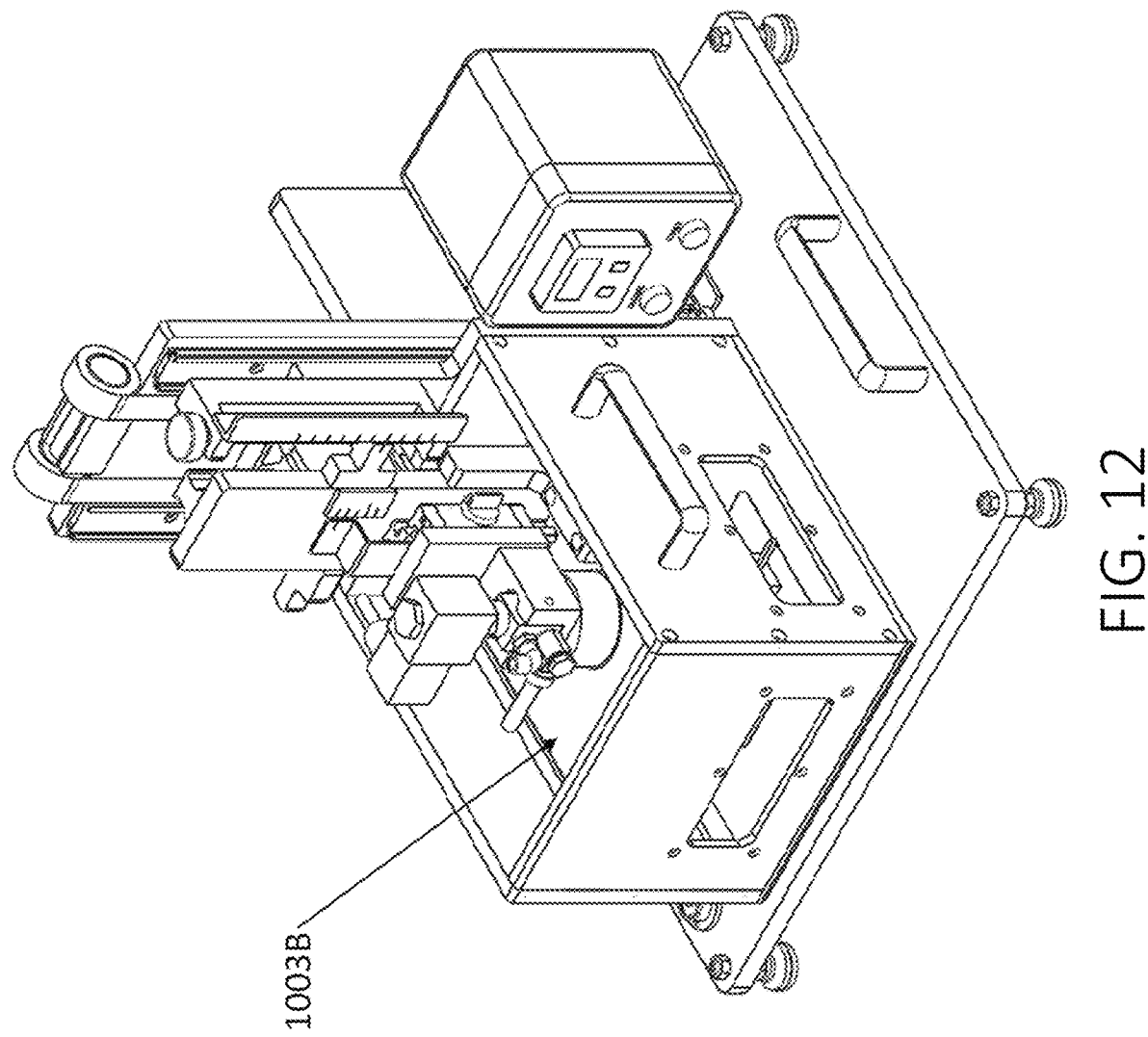
FIG. 12 illustrates an adjustable volume top plate in the down position of the automated deposition device of FIG. 1, in accordance with at least one example of the present disclosure.

FIG. 12 illustrates an adjustable volume top plate 1003B of the automated deposition device of FIG. 1. In the present configuration, the volume of the chamber is configurable by way of manipulating the height of the top plate with respect to the chamber via the rail 2003. In this and other configurations, the configurability of the volume of the chamber may be accomplished through a variety of approaches. Non-limiting examples include chambers with an adjustable threaded top, customizable sized chambers, and expandable and contractible chamber walls in all directions. The top plate is configurable in any position, non-limiting examples include 1 inch, 2 inches, 3 inches, 4 inches, 5 inches, 6 inches, 7 inches, 8 inches, 9 inches, 10 inches, or more. This volume can be adjusted at a variety of different points during operation of the system, non-limiting examples include in-between different target surfaces, in-between different inoculums to be deposited, during the same operation with the same inoculum, and between separate experiments example volume changes and quantities include: 100 $in^3$, 151 $in^3$, 200 $in^3$, 250 $in^3$, 270 $in^3$, 300 $in^3$, 350 $in^3$, 363 $in^3$, 389 $in^3$, or 400 $in^3$.

Figure 13A:
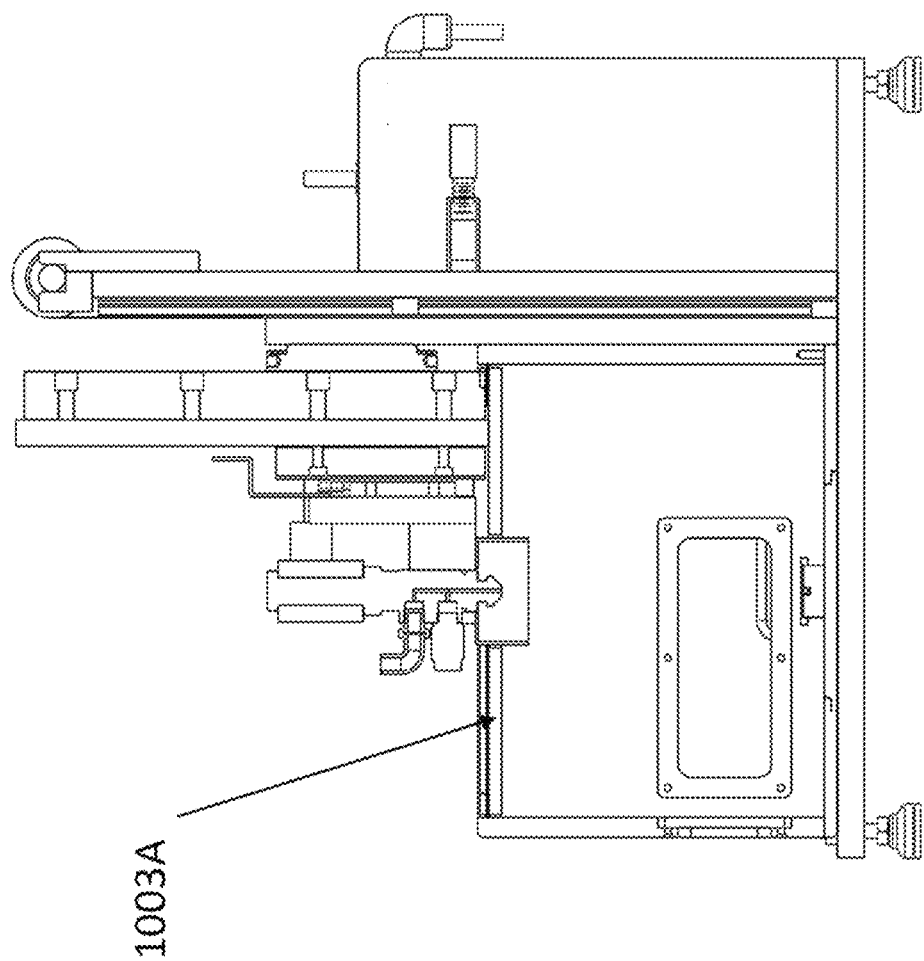
FIGS. 13A-13B illustrate a cross sectional view of the automated deposition device configured to different top plate heights and therefore different volumetric values, in accordance with at least one example of the present disclosure.
Figure 13B:
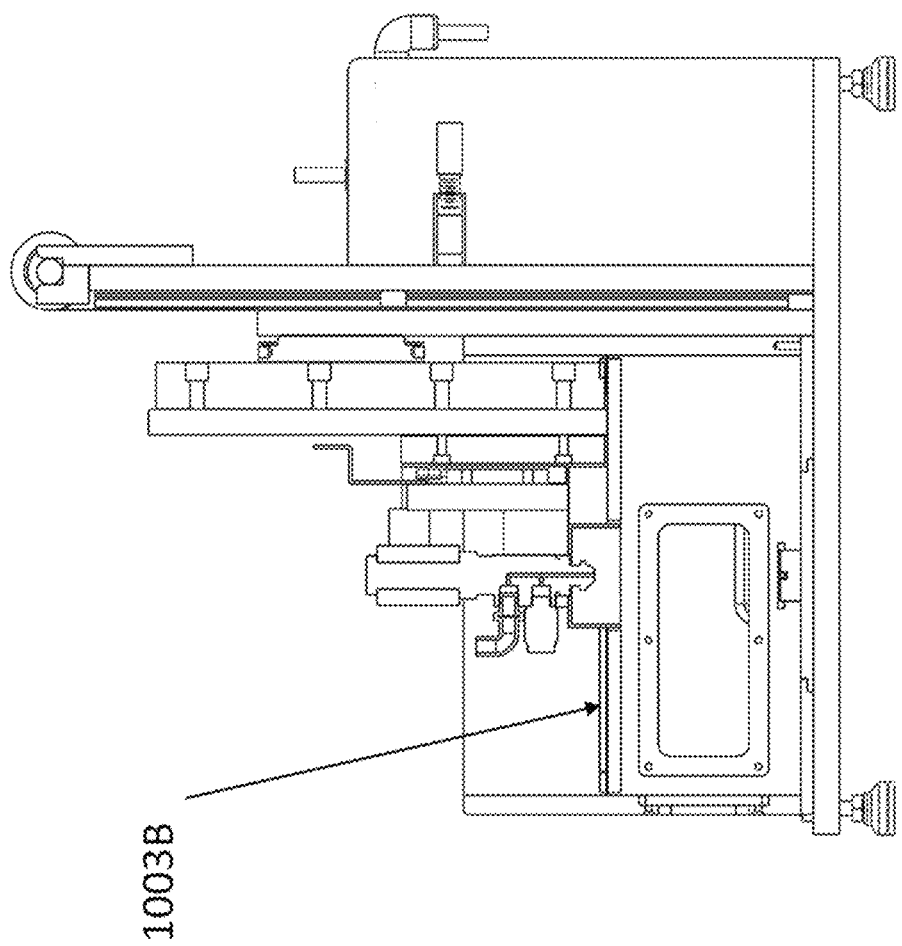

FIGS. 13A-13B illustrate a cross sectional view of the automated deposition device configured to different top plate heights and therefore different volumetric value. In this and other configurations, the horizontal alignment of the nozzle with respect to the stage and stage insert remains constant. Alternatively, the nozzle can be adjusted with respect to the top plate in order to produce different cone angle sizes of spray within the adjustable volume chamber. Cone angles can vary from very obtuse angles to very acute angles depending on the desired outcome.

FIG. 14 illustrates the removal or separation of the chamber of an automated deposition device of FIG. 1. In the present configuration, labeled 1000C, the chamber is fastened to the mounting plate by way of screws on the back side of the chamber. In this and other configurations, the chamber may be removable from the system through a variety of mechanisms. Non-limiting examples include clips, clamps, pins, bolts, hooks, straps, or detachable ratcheting mechanisms. This feature allows for a variety of different shapes, sizes, or types of chambers to be utilized within the system which can interact with the adjustable height top plate allowing for complete volumetric customization within the device. Different length and width chambers of varying sizes can be inserted into the system, while still adjusting the top plate to manipulate the volume of the chamber.

Figure 15:
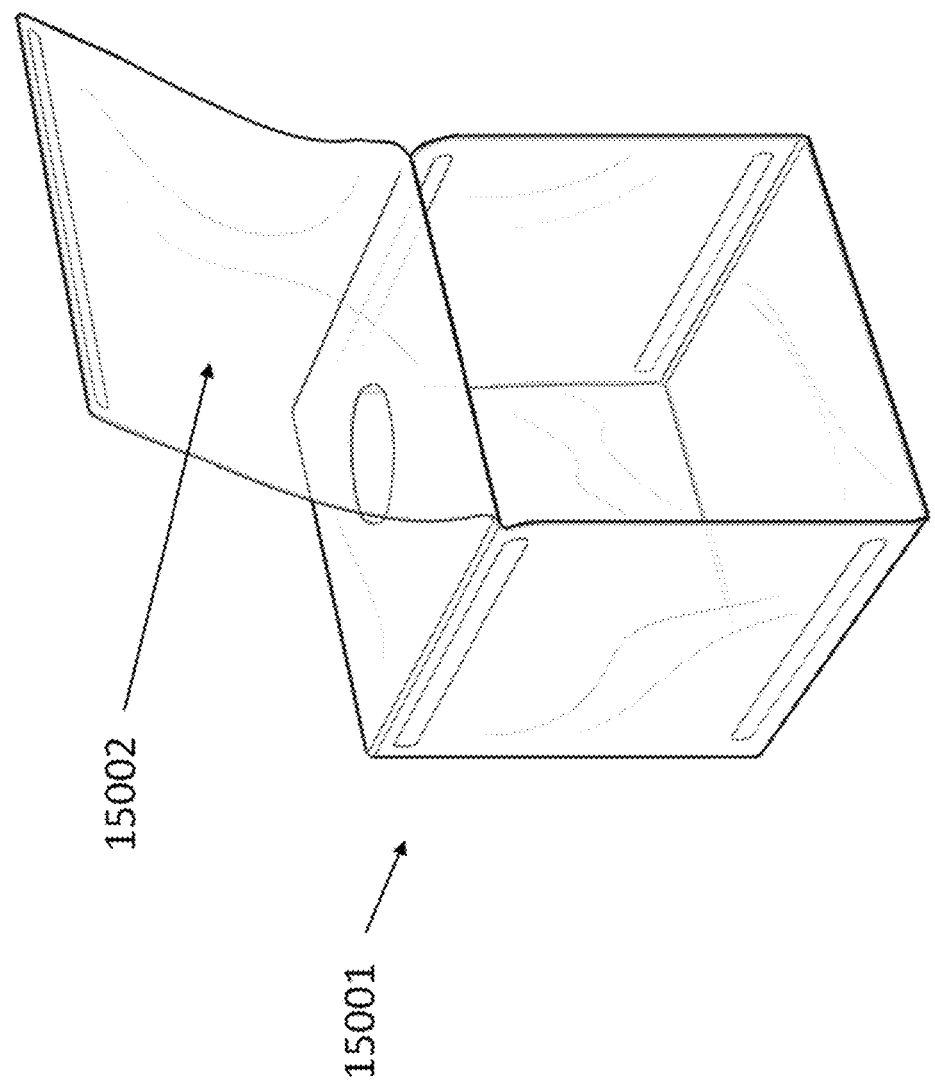
FIG. 15 illustrates a liner to be used for contamination or particulate control within the chamber of the automated deposition device, in accordance with at least one example of the present disclosure.

FIG. 15 illustrates a liner to be used for contamination control within the chamber of the automated deposition device. In the present configuration, a liner, 15001, with an openable flap door 15002, serves as a protective layer that may encapsulate and isolate the chamber, insert, stage, target surface mechanism, and top plate from the remainder of the deposition device's components. In this and other configurations, the liner and flap door may be used to aid in prevention of contamination or inadvertent particulate scatter caused by inadvertent spray on other device components. In this and other configurations, the liner may be easily removable such as to provide ease of decontamination, disinfection or disposal and replacement.

Figure 16:
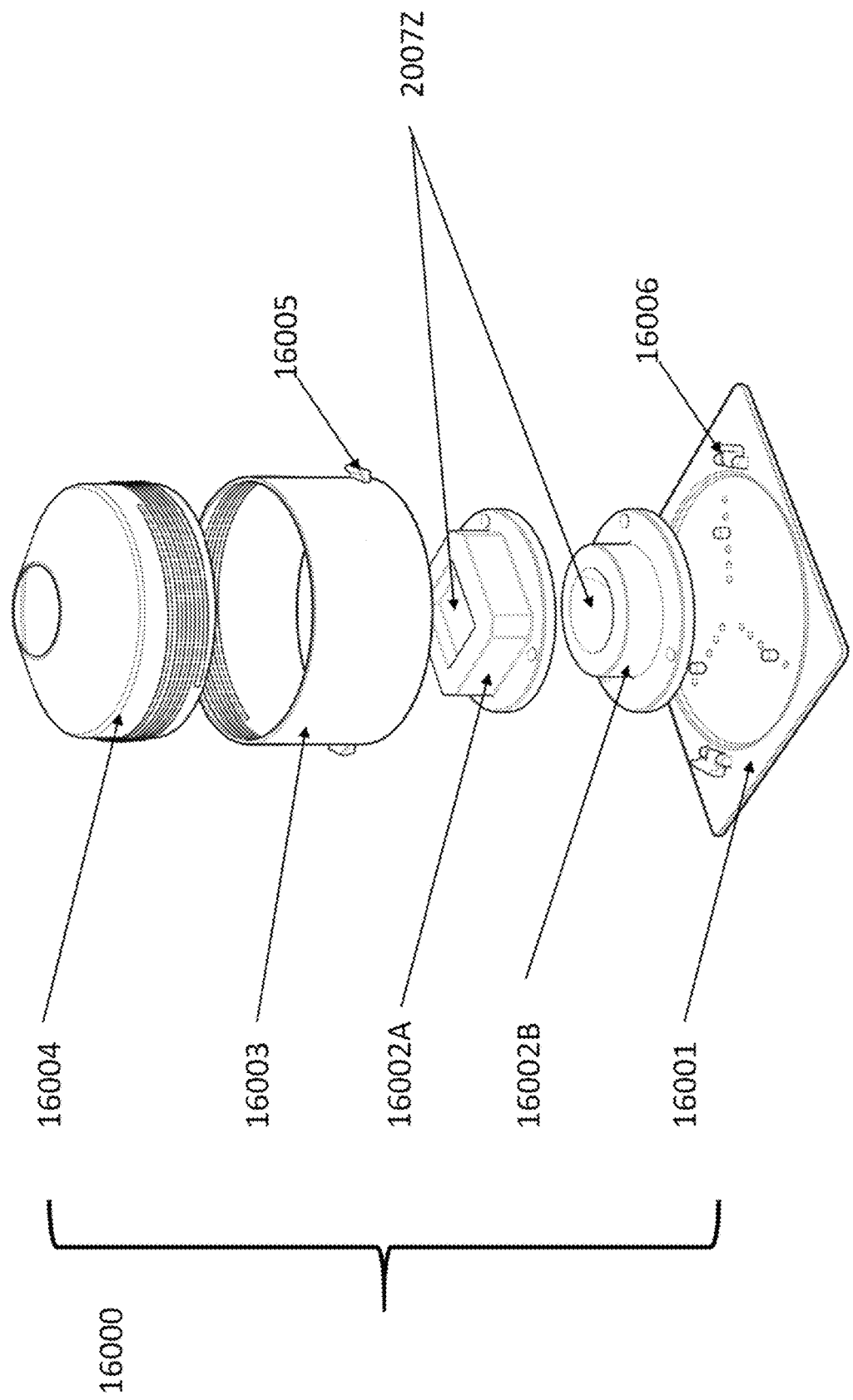
FIG. 16 illustrates an exploded view of another configuration of the volumetric chamber containing the stage, insert, and target surface mechanism, in accordance with at least one example of the present disclosure.

FIG. 16 illustrates an exploded view of an alternative chamber assembly 16000, stage 16001, stage insert 16002A or 16002B, and target surface depicted with two different geometries 2007Z. In the present configuration, the chamber is comprised of a top plate 16004, chamber 16003, and stage 16001. The top cap is operably coupled to the mid-wall by way of a top plate external threading and chamber internal threads. The chamber is operably coupled to the stage by way of hinged clamps 16006 present on the stage that fasten to extrusions 16005 on the chamber. In the present configuration, the volume of the chamber may be configured by tightening or loosening the thread interface between the top plate and chamber. The removal of the chamber may be accomplished by uncoupling the hinged clamps from the chamber extrusions. In the present configuration, there exists two different stage insert representations, 16002A and 16002B. The two configurations introduce the ability to accept various geometries of target surfaces dependent on the desired application. In this and other configurations, there are a variety of geometries of stage inserts dependent on that of the target surface. Non-limiting examples include rectangular, triangular, spherical, cubic, cylindrical, or irregular shaped inserts and thus stages. In the present configuration, the stage inserts, 16002A and 16002B, and the stage, 16001, have three alignment mechanisms present for ensuring repeated positioning of the stage and insert. In this and other configurations, there are a variety of mechanisms for repeated alignment of the stage with respect to the base tray. Non-limiting examples include pins, keyways, recessed grooves, visual indicators, or clamps.

Figure 17:
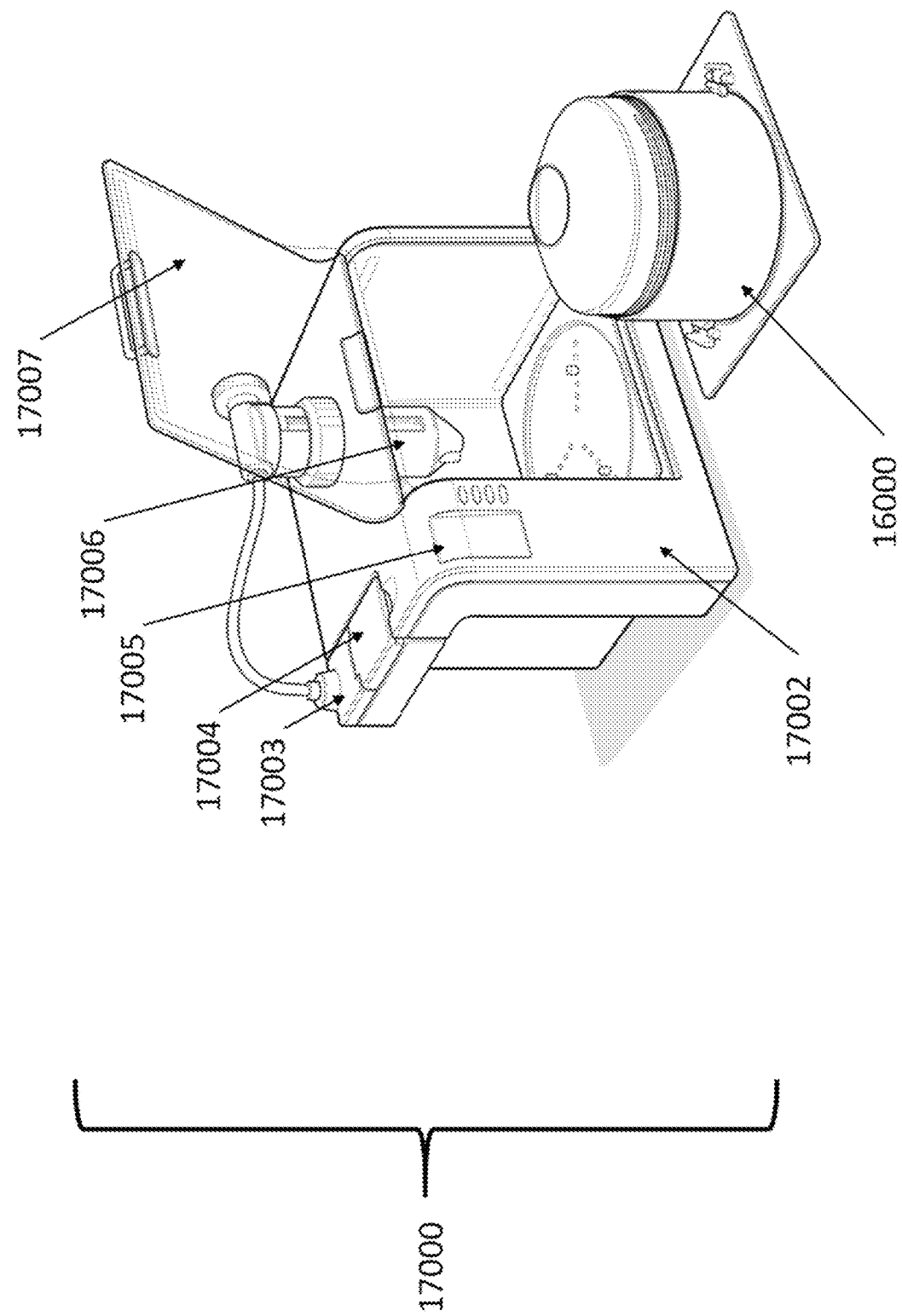
FIG. 17 illustrate a configuration of the automated deposition device, in accordance with at least one example of the present disclosure.

FIG. 17 illustrates a configuration of the automated deposition device 17000. In the present configuration, a variable-volume chamber, 16000, as described in FIG. 16, is comprised within an enclosed structure with a base, 17002. Within this enclosure resides a nozzle, 17006, of adjustable height. An access door, 17007 is present on the front side of the enclosure as well as a controller, 17005. A reservoir, 17003, is present in this configuration that provides solution to the nozzle for deposition operation. In this and other configurations, the reservoir for holding the deposition solution may have an access point or inlet 17004 intended for refilling the deposition solution. In this and other configurations, the reservoir and access point may be located in a variety of areas within the device. Non-limiting examples include on the nozzle head, behind the enclosure, at the base of the enclosure, above the nozzle, or below the controller.

Figure 18:
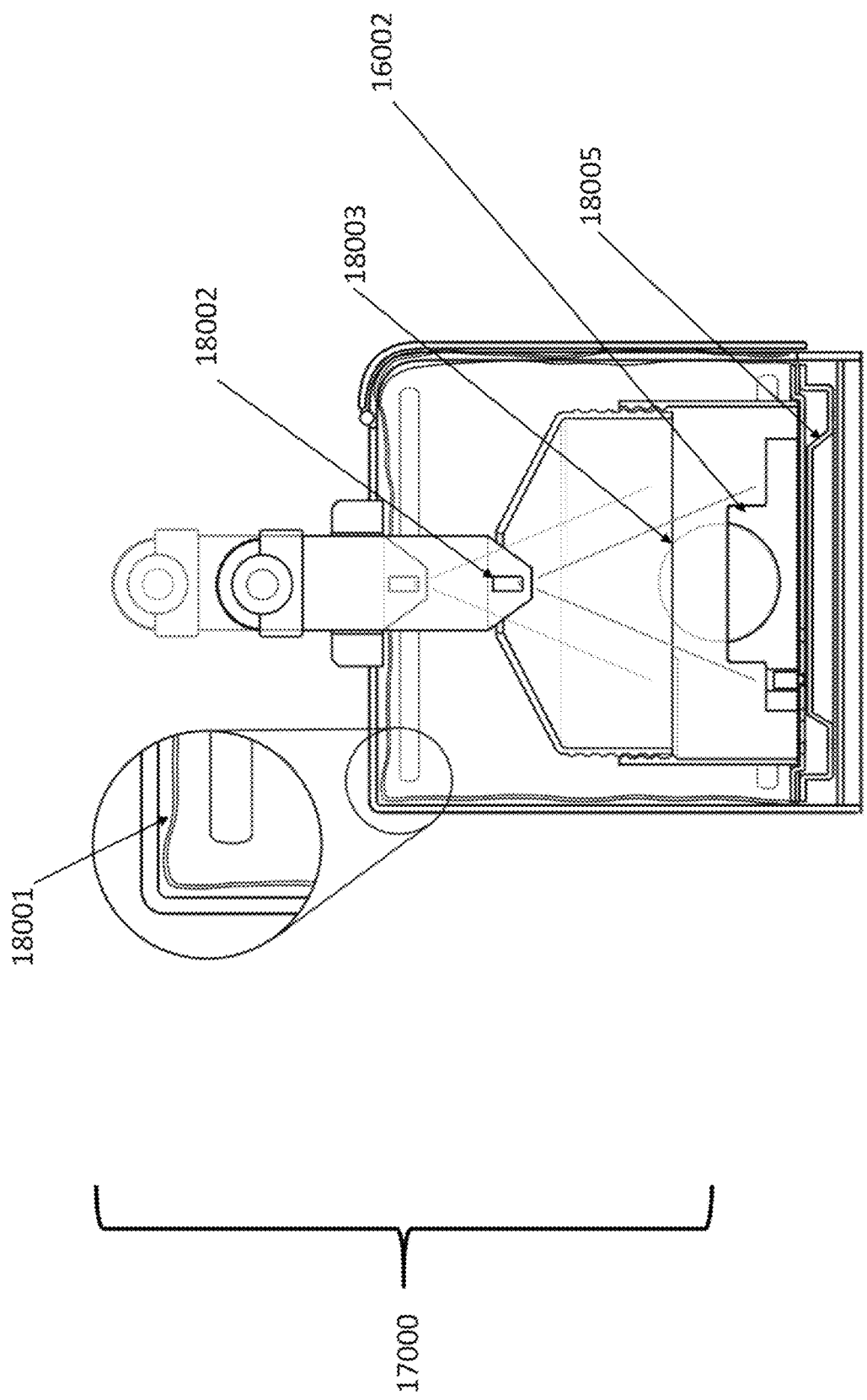
FIG. 18 illustrates the detailed cross-sectional view of the inner liner within the chamber of the automated deposition system, in accordance with at least one example of the present disclosure.

FIG. 18 illustrates a cross sectional view of the automated deposition system 17000 and detailed view of the liner within the chamber of the automated deposition system. In the present configuration, a removable liner, 18001, as described in FIG. 15, is present to provide protection for the system against inadvertent contamination. Additionally, a proximity/height sensor, 18002, is present on the adjustable height nozzle. In this configuration, the proximity/height sensor is intended to provide operator feedback via the controller as to the height, volume or distance to the target surface as well as other parameters such as chamber engagement and calibration capabilities of the nozzle with respect to the chamber, and the height of the chamber (and thus the volume) with respect to the system in a feedback loop of information in the calibration process of the deposition process. This can be a manual operation or an automatic programmable operation. Additionally, a stage insert 16002, is present within the chamber that holds a spherical target surface, 18003, for repeated acceptance of deposition. This target surface, 18003, is intended to be an alternate to the target surface, 2007, shown in FIG. 10. Furthermore, in this and other configurations, there may be a removable drip pan, 18005. The removable drip tray may serve as an added layer of protection similar to the liner that prevents inadvertent contamination. In this and other configurations, the removal of excess or overspray solution may be accomplished in a variety of ways. Non-limiting examples include a sloped pan, removable moat, interchangeable pooling channel, or base plate liner. Additionally, the base plate parts of the present configuration may all be easily removable for the purposes of periodic cleaning, disinfection, or disposal and replacement.

Figure 19A:
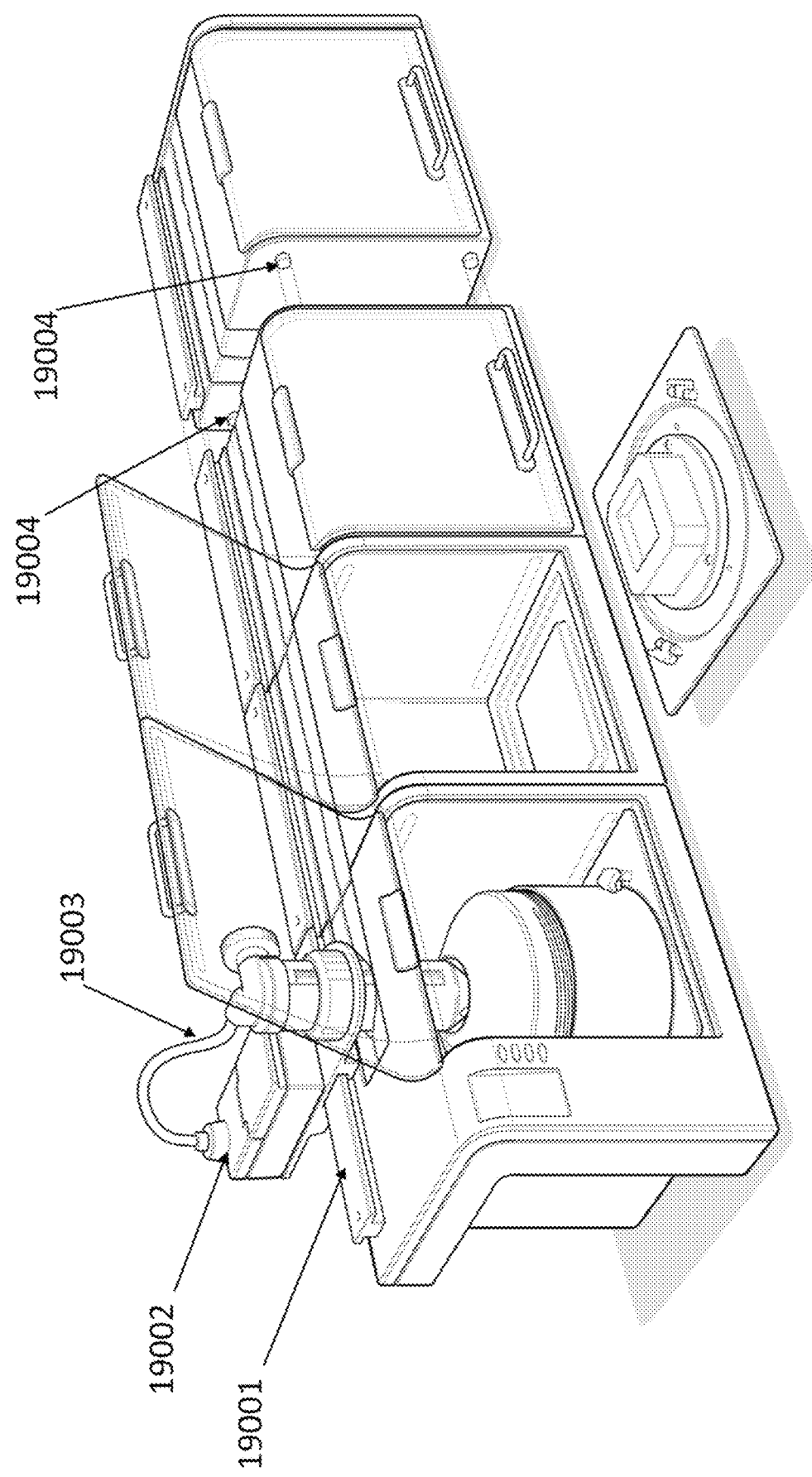
FIG. 19A-19B illustrates a configuration multi-chamber automated deposition system where the nozzle can travel on a track to multiple different chambers with adjustable volume, in accordance with at least one examples of the present disclosure.
Figure 19B:
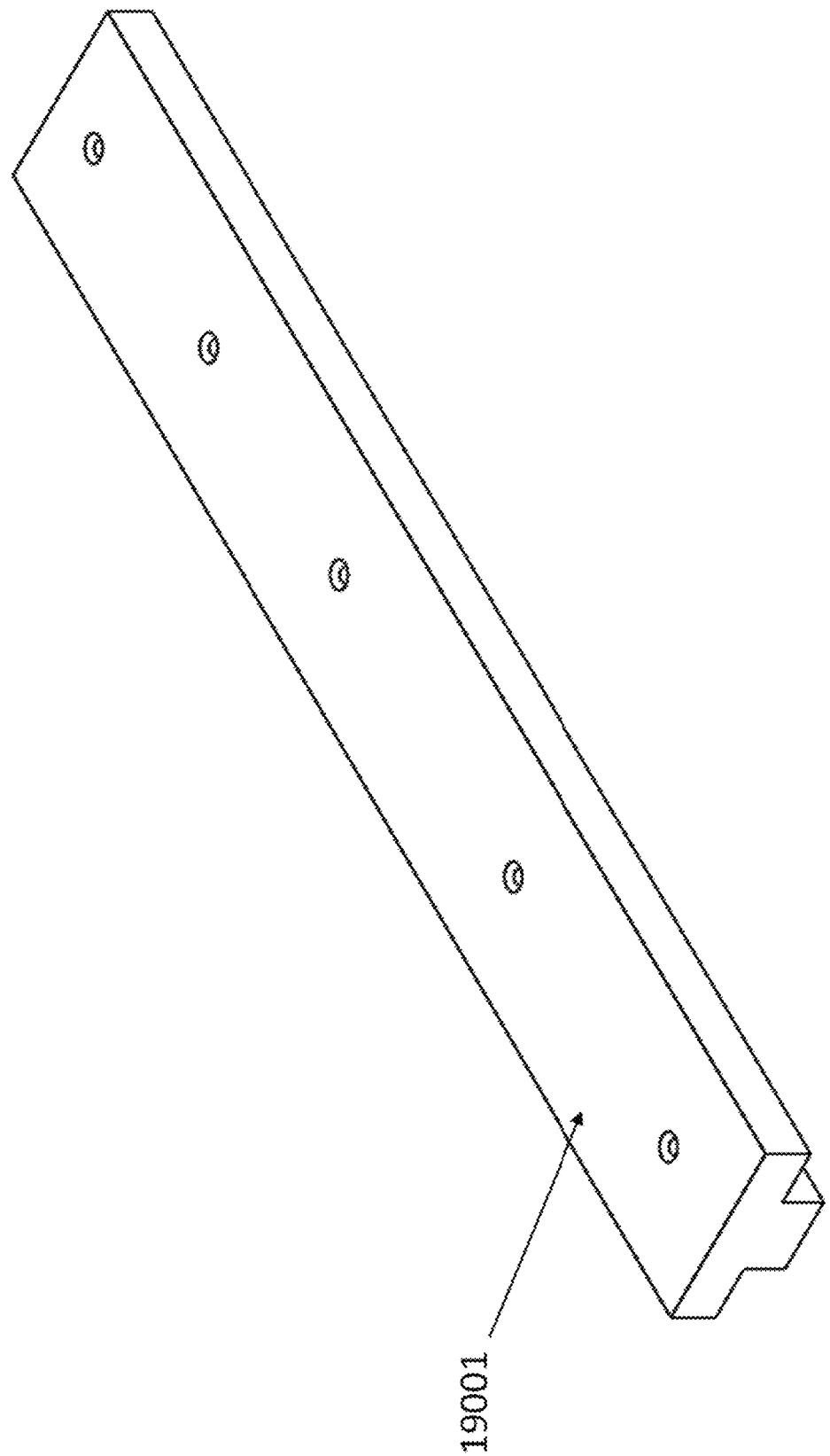

FIG. 19A illustrates a multi-chamber automated deposition system where the nozzle can travel on a track to multiple different chambers with adjustable volume. This configuration is an expansion of the configuration depicted in FIG. 17 and FIG. 18, in which multiple enclosures, 17002, may be coupled to each other to allow for multi-chamber automated deposition. In the present configuration, the nozzle track, 19001, which is further detailed in FIG. 19B, allows for the nozzle, 17006, to translate linearly along itself to move from one enclosure to another to perform a deposition operation. Similarly with FIG. 17 and FIG. 18, a sensor, 18002, is present within this configuration that introduces the ability for the controller, 17005, to relay information regarding height of the chamber with respect to the nozzle and the system, and thus the volume of the chamber as well as other parameter that can be detected and sensed by the programmable controller such as density, speed, volume, positioning and operational instructions for use such as a schedule. In this and other configurations, enclosures may be linked to each other via alignment features, 19004, present on the external surfaces of the enclosures. In this and other configurations, the enclosures may be aligned and linked by way of a variety of methods. Non-limiting examples include keyways, alignment rods, mechanical fasteners, guide rails, latches, magnetic locks, or ratcheted hooks. In this and other configurations, the nozzle, inlet hose, 19003, and reservoir, 19002, may require translation along the nozzle track together. In this and other configurations, similar to FIG. 17, an access point 17004 may be present, intended for refilling the deposition solution.

Figure 20A:
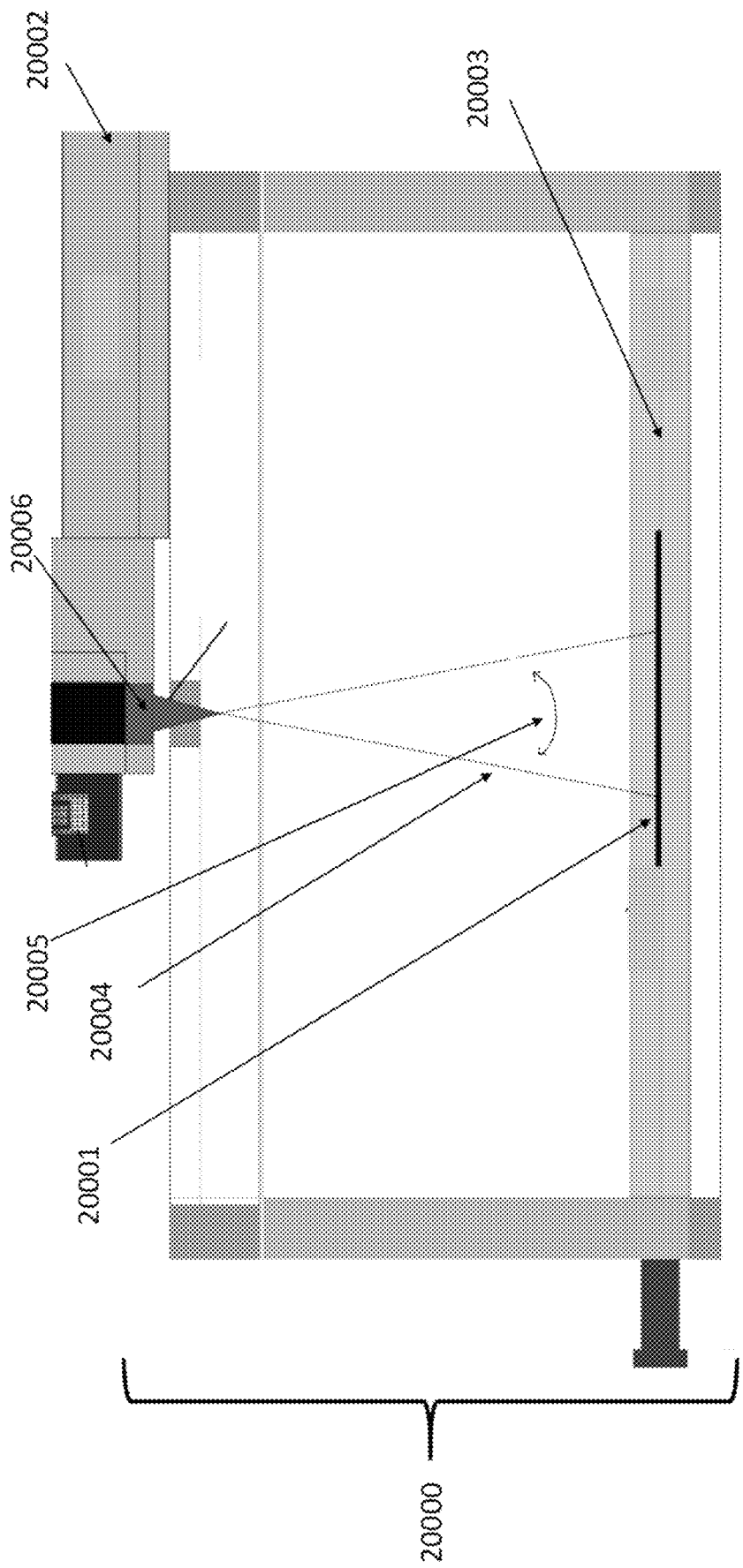
FIG. 20A-20C illustrates a cross sectional view of a configuration of the automated deposition device with tray access to the chamber and examples of controls with cone radius, in accordance with at least one example of the present disclosure.
Figure 20B:
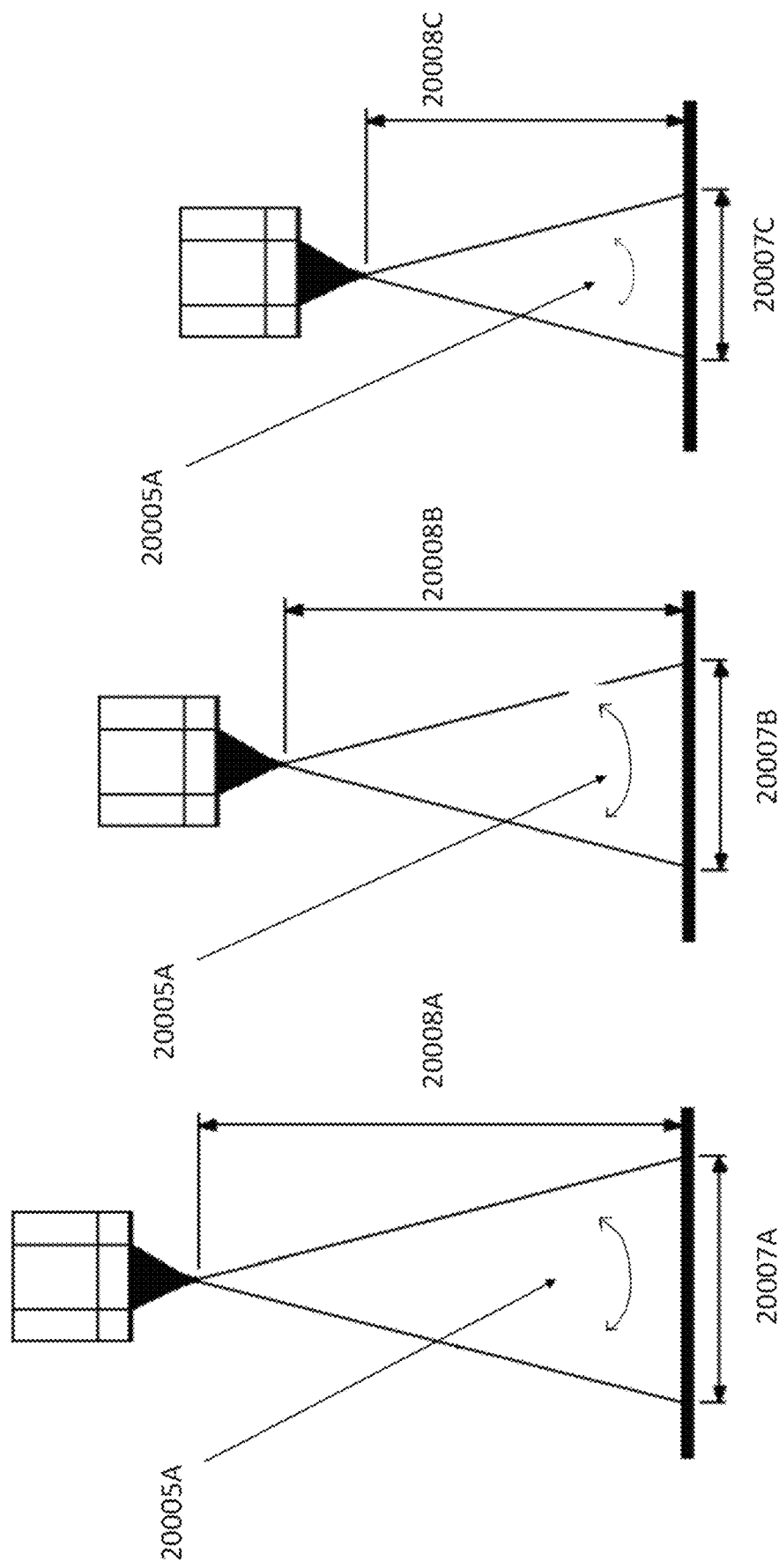
Figure 20C:
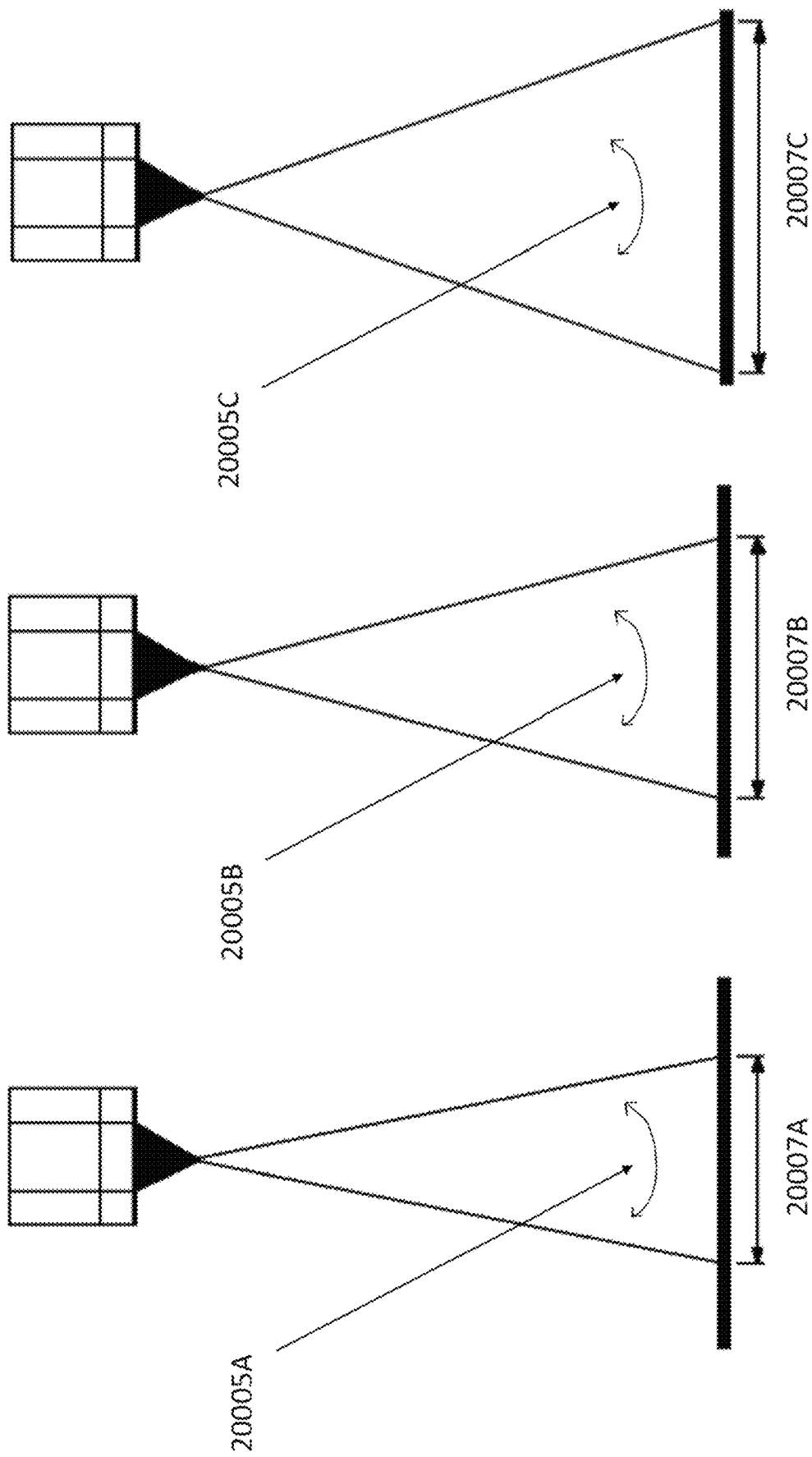

FIG. 20A illustrates a cross sectional view of a configuration of the automated deposition device 20000. This figure contains a target surface 20001, a nozzle holder 20002, a fixed base 20003, a Cone 20004 and cone angle 20005, and a nozzle 20006. In this and other configurations, as depicted by the cone angle, 20004, in FIG. 20B, the height of the nozzle or chamber with respect to the chamber and the target surface will determine the variable radius of spray of by the cone angle or by the height and volume of the chamber. Non-limiting examples of variable deposition radius while maintaining conical angle of spray include 0.750 inches, 0.850 inches, 0.900 inches, 1.000 inch, 1.146 inches, 1.500 inches, 1.718 inches, or 2.000 inches, or greater. The variation of the angle can change the spray radius and the amount of organisms being deposited in a particular area on the target surface. By adjusting the angle, a desired layer of the inoculant can be created on the target surface without overshooting or undershooting, for example, the desired level of deposit. FIG. 20B demonstrates that by keeping the cone angle 20005A the same value, then the change in chamber or nozzle height 20008A, 20008B and 20008C respectively can alter the spray radius 20007A, which is larger than spray radius 20007B, which is larger than spray radius 20007C. Similarly in FIG. 20C details an alternate approach for adjusting the radius of spray 20007C which is larger than 20007B which is larger than 20007A by controlling and adjusting the cone angles 20005C, 20005B and 20005A respectively upon the target surface. In addition to the height of the nozzle or chamber, the spray cone angle 20005, can be controlled via a setting within the nozzle for focused or wide-angle deposition depending on the target surface or object. Non-limiting examples of the nozzle cone angle include 5 degrees, 15 degrees, 25 degrees, 35 degrees, 45 degrees, 55 degrees. 65 degrees, 75 degrees, 90 degrees. In this and other configurations, the nozzle and inlet for the nozzle may be capable of accommodating various types of liquids with various sizes of microorganisms of different concentration. Non-limiting examples include *Staphylococcus aureus*, Methicillin resistant *Staphylococcus aureus* (MRSA), Vancomycin resistant *enterococcus* (VRE), *Pseudomonas aeruginosa, Acinetobacter, Clostridium difficile, Escherichia coli*, and *Klebsiella pneumoniae*.

FIG. 21 illustrates an application for the automated deposition device for testing light-based disinfection technology. The automated deposition system has the capability to deposit bacteria, spores, funji, viruses, or any other microorganisms in a uniform, controlled manner, depositing a monolayer of cells on the target surface. This can then be applied for standardized testing of disinfection methods for these microorganisms as the different testing variables can all be controlled and repeated consistently with this system. Non-limiting testing variable examples include type of microorganism, organism inoculum concentration, material of the target surface, shape of the target surface, size of the target surface, inoculum liquid solution, and inoculum contamination control. With control over these parameters it is possible to reliably apply microorganisms to target surfaces and directly compare the efficacy of non-chemical-based disinfection, or sterilization systems. Non-limiting examples of non-chemical bases disinfection or sterilization technology include ultraviolet-C, gamma rays, x-rays, blue light, or far-UV. The target surfaces can be exposed to the light technology at a specific height or table, 21001, within the testing systems and validated for reduction of organisms on a selected surface. 21002 is an example of a testing system utilizing FMUV technology within a large chamber to treat surfaces for the purposes of disinfection.

Figure 22:
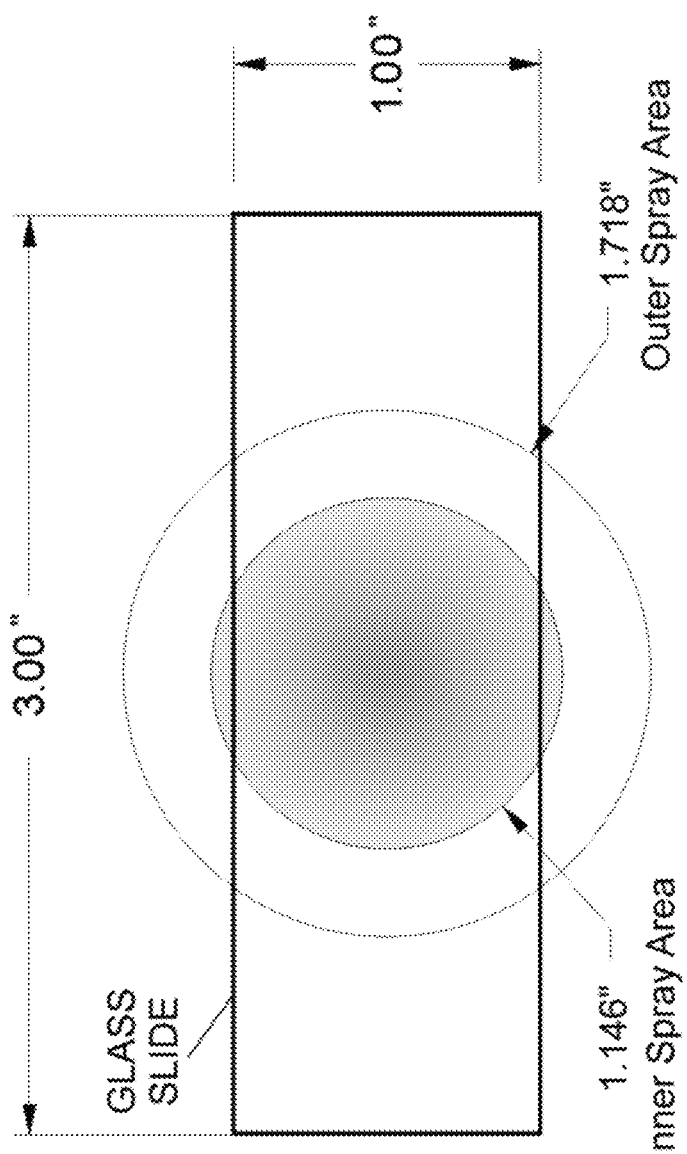
FIG. 22 illustrates a configuration of a target surface and how the automated deposition device would deposit specimens on a surface, in accordance with at least one example of the present disclosure.

FIG. 22 illustrates a configuration of a target surface and how the automated deposition device would deposit specimens on this surface. In this and other configurations, radius of spray may be controlled by way of various methods. A mechanism for controlling the height of the chamber or nozzle with respect to the stage insert or target surface may vary the radius of spray of the solution without changing the conical angle of spray. Alternatively, the nozzle may be adjusted to configure conical radius of spray without adjusting the height of the nozzle with respect to the carrier. Both of these variables are configurable within the adjustable volume chamber within the overall automated deposition system.

Figure 23:
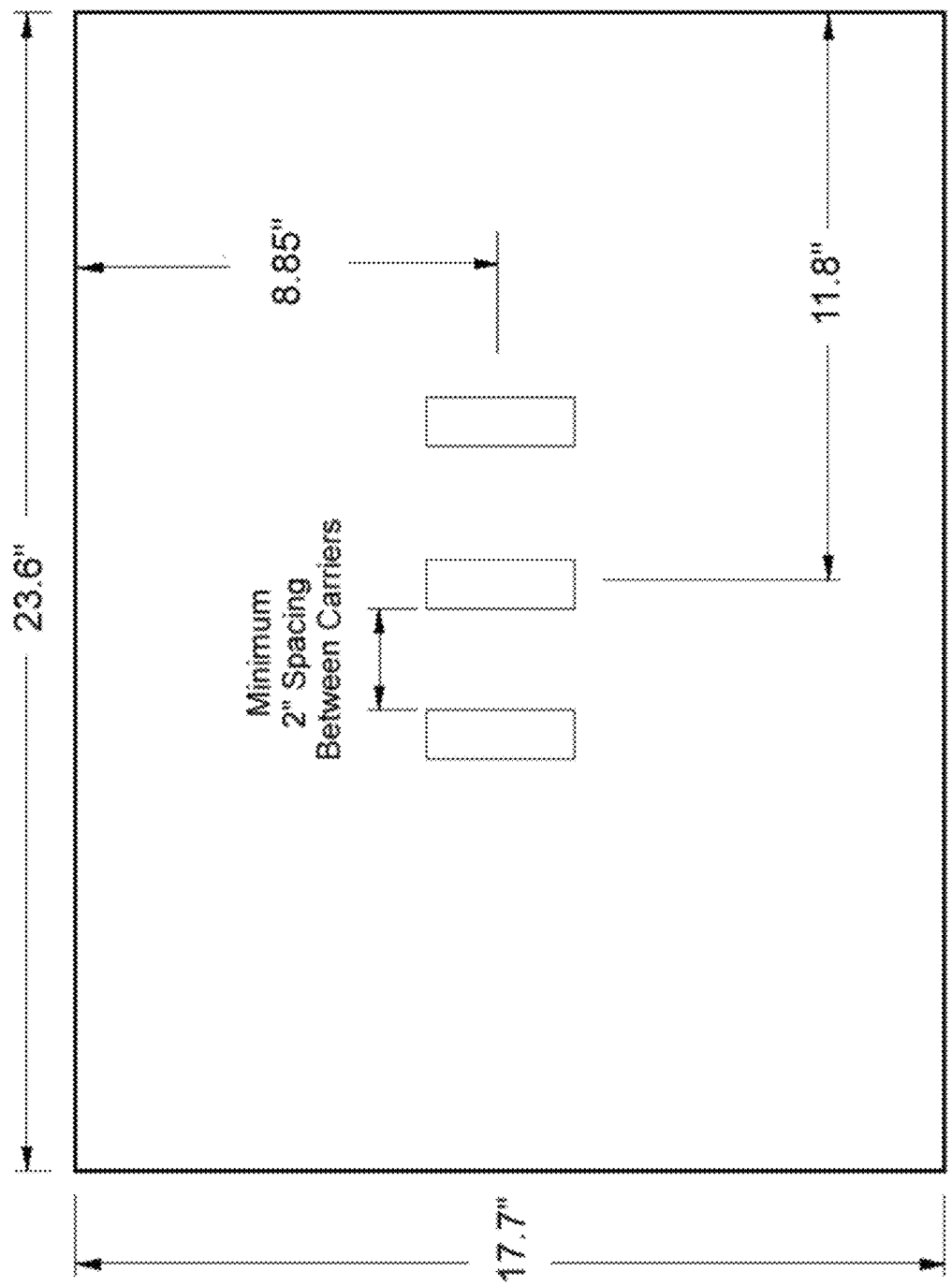
FIG. 23 illustrates a placement of the target surface of FIG. 22 to be used for testing such surfaces, in accordance with at least one example of the present disclosure.

FIG. 23 illustrates a placement of the target surface of FIG. 22 to be used for testing such surfaces and exposing the target surface to light-based disinfection and or non-ionizing radiation. In this configuration, the configuration in FIG. 19 may be utilized in junction to incorporate efficient, simultaneous multi-surface testing. These configurations may minimize the interval of time witnessed between placing target surfaces or inserts into a testing apparatus, and thus may improve experimental outcome and reliability. Multiple target surfaces may be exposed to disinfection technologies for the purposes of reviewed and testing efficacy of those systems. Due to the nature of light-based technologies, in some testing setups the target surfaces need to be 0.5 inches, 1 inch, 2 inches, 3 inches, or more apart from one another. Furthermore utilizing the multi-chambered configuration of FIG. 19 can then be tested simultaneously within a non-chemical based disinfection system, 1, 2, 3, 4, 5, 6, 7, 8, 9, 10, 11, 12 or more target surfaces may be testing at the same time within a disinfection system.

Figure 24:
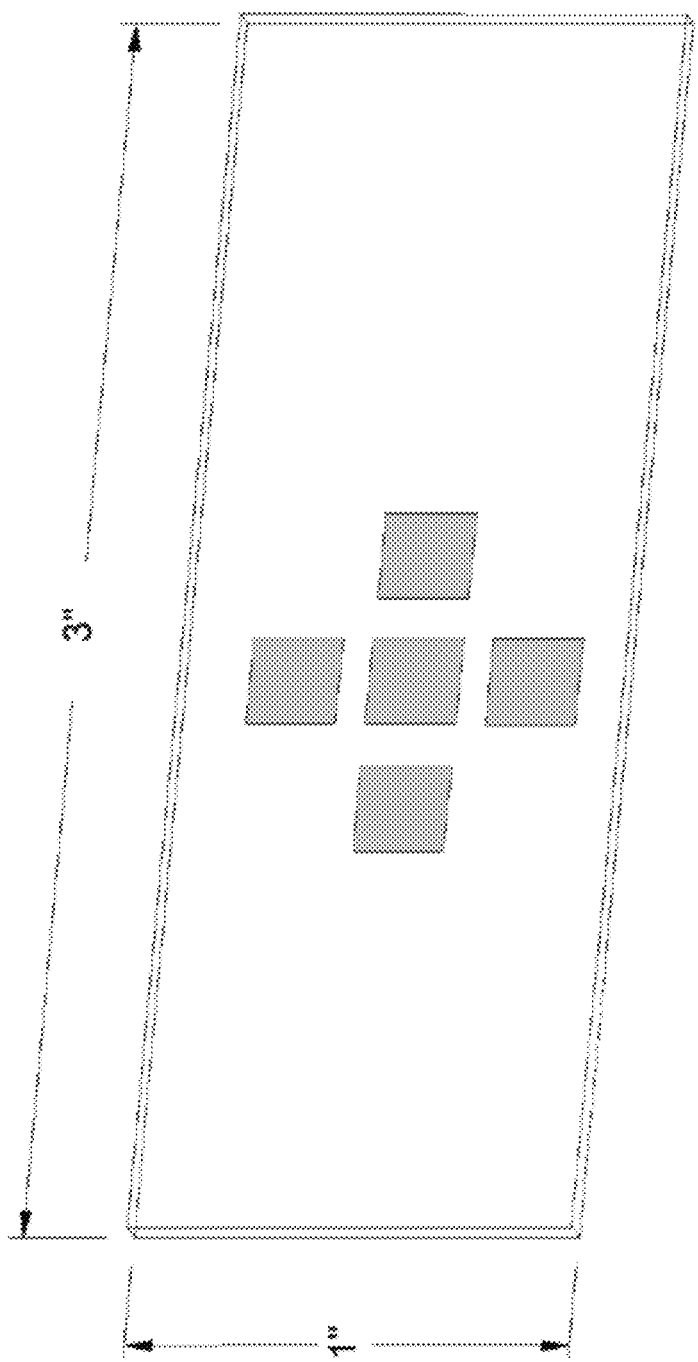
FIG. 24 illustrates locations for microscopic imaging the target surface to confirm automated deposition system microfilm and deposition, in accordance with at least one example of the present disclosure.

FIG. 24 illustrates locations for microscopic imaging the target surface to confirm automated deposition system performance. The automated deposition system utilizes an adjustable nozzle 1004 to aerosolize organisms onto a target surface. The 3-tiered adjustable chamber as depicted in FIG. 2 and FIG. 12 can be manipulated by the following non-limiting examples: nozzle height, nozzle cone angle, nozzle spray radius, chamber height, chamber volume, chamber shape, chamber size. To determine the microbiological effects of these different parameters, target surfaces can be imaged at a microscopic level. Non-limiting examples of microscopic imaging include compound light microscope, scanning electron microscope, stereo microscope, scanning probe microscope, or fluorescence imaging.

FIG. 25A illustrates lab testing results of ultraviolet disinfection system validating using target surfaces treated with the automated deposition device and *Staphylococcus aureus*. FIG. 25B illustrates lab testing results of ultraviolet disinfection system validating using target surfaces treated with the automated deposition device and *Pseudomonas aeruginosa*.

Materials and Methods: Bacterial samples were inoculated onto carriers using an automated inoculum deposition system as described in the following sections.

CARRIER PREPARATION: Carriers were prepared in accordance with EPA Standard. New carriers were soaked in a detergent solution for 1 h-2 h to degrease and were washed and rinsed thoroughly with de-ionized water. All carriers were checked for pitting or other damage under a dissecting microscope. Damaged carriers were discarded.

The acceptable carriers were stacked in a beaker between sheets of filter paper and autoclaved. The whole set of carriers was autoclaved for 45 minutes at 121° C. After sterilization, the whole set of carriers were kept in a biological safety cabinet and were allowed to cool down to room temperature. Once the bacterial working solution was ready to use, the carriers were taken out and set up in sterile petri dishes.

INOCULANT PREPARATION: Standard anchor microorganisms were used in this study, *Staphylococcus aureus* (ATCC 6538) and *Pseudomonas aeruginosa* (ATCC 15442) and were prepared in accordance with the methods described in EPA Standard Operating Procedure. For each microorganism, a single frozen cryovial of stock culture was defrosted at room temperature and then briefly vortexed to mix. A 10 µL aliquot of the thawed stock was added to a tube containing 10 mL of either Synthetic Broth (SB) media for *S. aureus* or Nutrient Broth (NB) media for *P. aeruginosa*. The tubes were vortexed for 3-4 sec and incubated at 36±1° C. for 24±2 hours. Daily transfers were made for at least one but for no more than five consecutive days.

For the final subculture transfer, a sufficient number of 20×150 mm tubes containing 10 mL of TSB were inoculated with 10 μL of culture per tube, vortexed to mix, and then incubated at 36±1° C. for 48 h-54 h. The 48 h cultures were not shaken.

For *Pseudomonas aeruginosa*: For the final subculture transfer, a sufficient number of 20×150 mm tubes containing 10 mL NB will be inoculated with 10 mL of culture per and incubated at 36±1 C for 48-54 h. At the completion of the 48 h-54 h incubation, the tubes were not shaken. The pellicle was removed by gently aspirating it away from the broth using a pipette, or by vacuum removal. Care was taken to avoid harvesting the pellicle from the bottom of the tube. No culture was utilized in testing in which the pellicle was disrupted. Test cultures were pooled from each tube and visually inspected to ensure there were no pellicle fragments because the presence of any pellicle fragments would have rendered the culture unusable for testing.

Each tube of inoculum was agitated on a Vortex-type mixer for 3-4 seconds, and then allowed to sit for 10 minutes. The upper portion of each culture was removed, leaving any debris or clumps, and transferred to a sterile flask, pooled, and swirled to mix. The prepared purified bacterial suspension was stored in small aliquots (e.g. 500 μL) in cryovials at approximately −20° C. for up to 1 year for use in testing. Before use for inoculation, the bacteria were washed and resuspended in deionized water. At least 1.5 mL of each bacterial suspension were required for each test, at concentrations of at least $10^9$ viable cells/mL.

Test Bacterial Suspension Acceptability Criteria

The bacterial suspension was considered acceptable for use if the following two criteria had been met:

The bacterial titer was at least $10^9$ viable cells/mL

Bacterial cell purity was greater than or equal to 95%

It was estimated that an inoculant concentration of $10^9$ CFU/mL would be sufficient to achieve a deposition rate $10^6$ CFU per carrier.

Automated Inoculum Deposition

The carriers were inoculated with an automated inoculum deposition system that was used to generate homogenous deposition of microorganisms on the carriers.[5] The unit consists of a mounting base plate with an arm supporting a high-precision two-substance 230 V, 50 Hz Model 970-8 magnetic nozzle (Schlick, Untersiemau, Germany), a liquid inlet receiver, a microprocessor-based quartz counter, an N2 source (nitrogen tank) with a pressure regulator, a spray chamber, a power switch and associated tubing and wiring. The features of this device can advantageously include: 1) It automates the quantity of bacteria, 2) It creates an even distribution with a monolayer, 3) Has a controlled bacteria concentration, a controlled amount of inoculant, and controlled media (deionized water).

The power switch and timer are used to synchronize the opening of the N2 inlet and the liquid inlet of the magnetic valve. The $N_2$ gas supply was regulated with a pressure gauge and a power-driven 3/2 magnetic valve between the gas supply and the nozzle air inlet. The spray radius was adjusted via the air cap of the nozzle which had 6 settings, 0 through 5, with 5 producing the widest angle of dispersion. During the test, the nozzle was at setting 5.

All automated inoculum deposition system components were either autoclaved or disinfected with a 70% isopropyl alcohol solution. The entire assembly was placed inside a Biological Safety Cabinet in a Biosafety Level 2 (BSL2) laboratory. The spray was directed through a hole in the top of a spray chamber as depicted in FIG. 20.

Approximately 200 μL of inoculant was pipetted into the receiver until it was full. Each carrier was placed inside the spray chamber using sterile forceps and centered below the spray nozzle. The switch was operated to spray once on each carrier. After a few seconds the carrier was visually inspected to verify that a thin film had been sprayed. The carrier was then removed and placed in a Petri dish using sterile forceps.

Once all the carriers were inoculated, they were placed in a vacuum chamber to air dry at room temperature for 2 hours.

Automated Inoculum Deposition Protocol

1. Defrost the cell-containing cryovial at room temperature.
2. Sterilize the component valves and the nozzle in an autoclave.
3. Wipe down all components of the Automated Inoculum Deposition system using 70% isopropyl alcohol.
4. Assemble the Automated Inoculum Deposition system.
5. Place the Automated Inoculum Deposition system inside a Biological Safety Cabinet in a Biosafety Level 2 (BSL2) laboratory.
6. Check the tank pressure gauge to verify an N2 pressure of $2 \times 10^5$ Pa (29 psig).
7. Set the nozzle head setting at 5.
8. Position the spray nozzle above the base of the spray chamber with the arm in direct contact with the top of the spray chamber.
9. Place blotter paper (in place of the glass slides) inside the spray chamber to absorb water.
10. Transfer about 10 μL of deionized water to the Inlet Receiver (see FIG. 1) to prime the spray nozzle and wet the internal surfaces.
11. Spray several times until the Inlet Receiver has been evacuated.
12. Remove the blotter paper from the spray chamber.
13. Use a pipette to take some 200 μL of inoculum from the cryovial.
14. Use the pipette to transfer inoculum to the inlet receiver until it is full (approximately 200 μL).
15. Using long metal tweezers, take up a carrier and pass it through the flame of a Bunsen burner for 1-2 seconds to slightly heat the carrier to remove any oils or possible film on the glass carrier. The carrier was allowed to cool for 3 seconds prior to inoculation.
16. Using sterile forceps, place one glass slide carrier inside the spray chamber centered below the nozzle using the surface-engraved grid axes or a mounted bracket as a guide (see FIG. 2 and FIG. 3).
17. Flip the switch once to run a single spray.
18. Visually verify that the sprayed cell suspension formed a thin film on the glass slide that dried within seconds.
19. Proceed with inoculating each glass slide carrier until the full set of carriers required have been inoculated.
20. Refill the inlet receiver approximately every three sprays to ensure an adequate level of fluid is always available for spraying.
21. Remove each inoculated glass slide and place it in a Petri dish.
22. Place all the Petri dishes with glass slides in a vacuum chamber to air dry for 2 h.

Ultraviolet Inactivation

A focused multivector ultraviolet (FMUV) system was used to treat the test carriers. The FMUV system consisted of four modular vertical panels that were arranged to enclose a central target zone as depicted in FIG. 21, and within the enclosed volume the ultraviolet irradiance is confined and maintained at high levels. Ambient temperature was verified to be in the normal indoor range (20-25° C.) and the ambient relative humidity was below 65%. Prior to performing each test run, a 90-second warmup cycle was performed. Following the warmup cycle (within 7 minutes), the carriers were placed on large glass plate on a table centered (26" from the walls) within the FMUV system at a height of 20 in. The height of 20" was based on minimum estimates for table and bed heights in hospitals. The minimum spacing between the three carriers was 2" as shown in FIG. 23. The device was closed and the 90-second test cycle was run immediately. Following the test cycle, the carriers were transferred into vials containing Letheen Broth (LB), utilizing sterile forceps for processing.

Enumeration of Colony Counts

Carriers were enumerated by an independent third-party laboratory. All plates were incubated under anoxic conditions at 36±1° C. All plates were enumerated, and the results were recorded at 48±1 h of incubation. All Test and Control carriers were inspected at 24 h to ensure that there was no overgrowth. If excessive growth did occur, then the plates were counted. If no or fewer than 10 colonies are observed at 48 h, plates were incubated for 24 additional hours before being counted. A selective media, MCA (MacConkey Agar), was used for growing the cultures for the gram-negative bacteria P. aeruginosa. The results will include the mean CFU per carrier and the mean log per carrier for both the Test and Control carriers for each microorganism.

Results

FIG. 25A summarizes the data for *Staphylococcus aureus*. The Mean Log 10 Density was calculated as the mean across the three Test or Control values of the log 10 density, in accordance with testing standards. For the Test 3 carrier which exhibited no growth a Limit of Detection (LOD) value of half (LOD/2) or 9 CFU/carrier was used in place of the LOD value (18 CFU/carrier), which is conservative in this case and which is one of several approaches for handling data below the LOD. In order to show the full range of the percent reduction a value of 0 was additionally used to calculate the reduction in the organisms. The control carriers had a mean log density of 6.1. There was an overall log reduction for *Staphylococcus aureus* of 4.8 when utilizing a LOD of 9 CFU/carrier, and there was an overall log reduction of 5.1 when a value of 0 was used for the test 3 carrier with no growth. This is calculated by looking at the difference between the control carriers and the FMUV treated carriers. The average percent reduction was determined to be between 99.9984-99.9992%

FIG. 25B summarizes the data for *Pseudomonas aeruginosa*. The Mean Log 10 Density was calculated as the mean across the three values for the log 10 density, for both the test carriers and the control carriers, in accordance with testing standards. For the Test 1 & 3 carriers which exhibited no growth, a Limit of Detection (LOD) value of half (LOD/2) or 9 CFU/carrier was used in place of the LOD value (18 CFU/carrier), which is conservative in this case and which is one of several approaches for handling data below the LOD. In order to show the full range of the percent reduction a value of 0 was additionally used to calculate the reduction in the organisms. The control carriers had a mean log density of 6.3. There was an overall log reduction of 5.1 when utilizing a LOD of 9 CFU/carrier, and there was an overall log reduction of 5.7 when a value of 0 was used for the test 1 & 3 carriers with no growth. This is calculated by looking at the difference between the control carriers and the FMUV treated carriers. The average percent reduction was determined to be between 99.9992-99.9998%.

Figure 26:
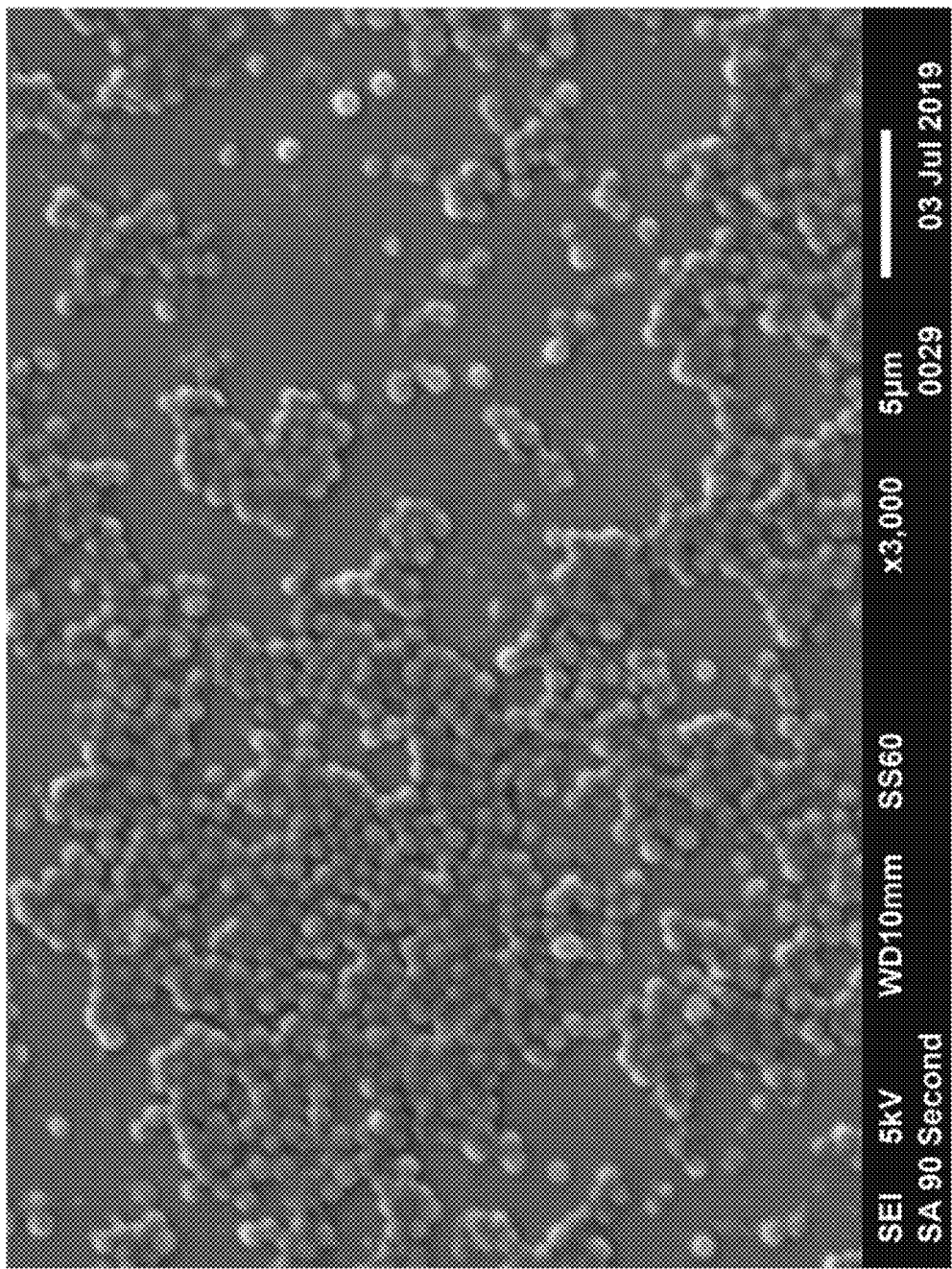
FIG. 26 illustrate scanning electron microscope (SEM) imaging of target surfaces deposited with organisms utilizing the automated deposition device and other methods, in accordance with at least one example of the present disclosure.

FIG. 26 illustrates an example of a scanning electron microscope (SEM) imaging of target surfaces deposited with organisms utilizing the automated deposition device. Different organisms can be utilized for automated deposition, non-limiting examples include *Staphylococcus aureus*, Methicillin resistant *Staphylococcus aureus* (MRSA), Vancomycin resistant *enterococcus* (VRE), *Pseudomonas aeruginosa, Acinetobacter, Clostridium difficile, Escherichia coli*, and *Klebsiella pneumoniae* or other organisms.

Figure 27:
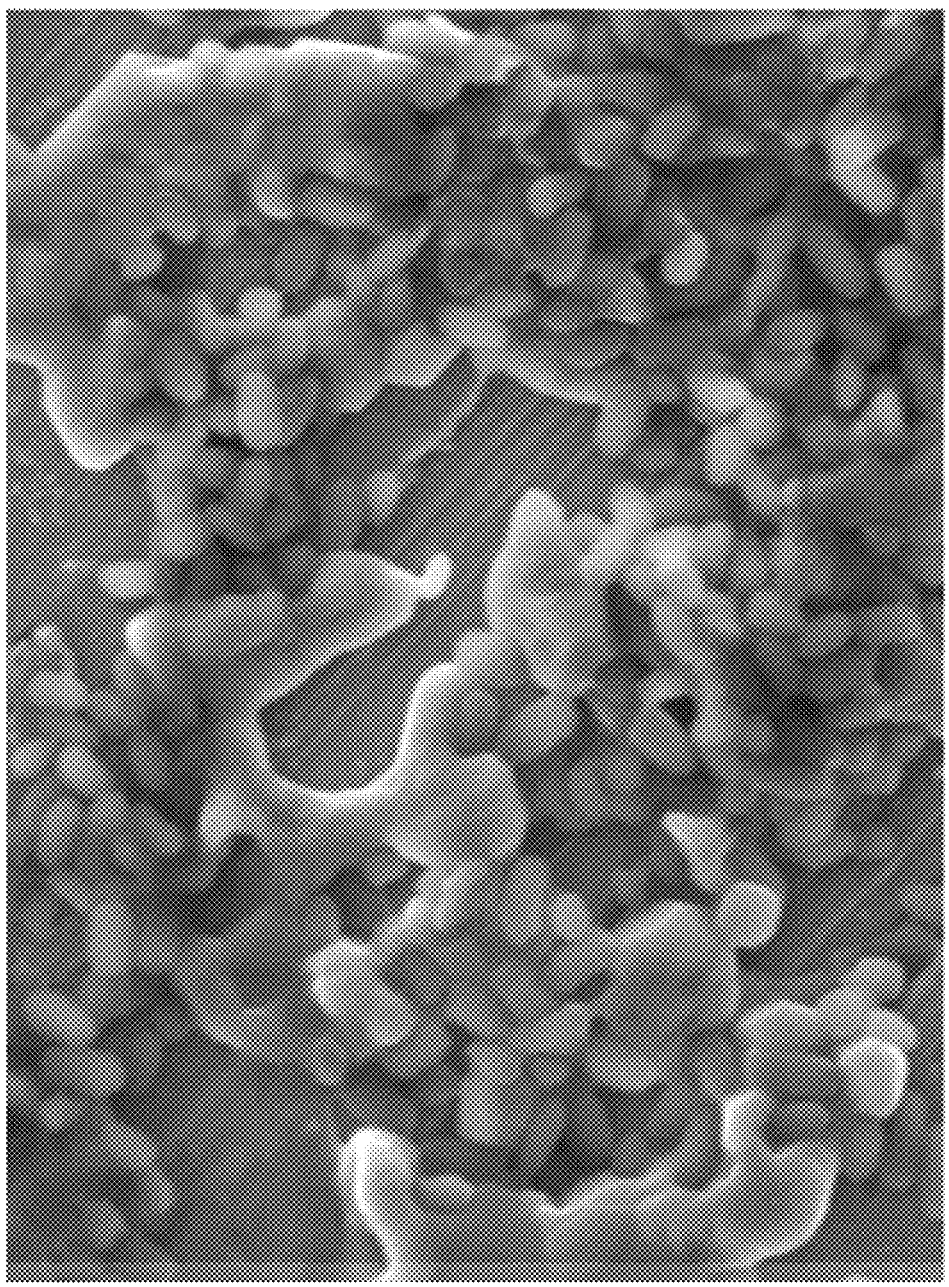
FIG. 27 illustrate scanning electron microscope (SEM) imaging of target surfaces deposited with organisms without utilizing the automated deposition device and other methods, in accordance with at least one example of the present disclosure.

FIG. 27 illustrate scanning electron microscope (SEM) imaging of target surfaces deposited with organisms when using a manual technique that shows clustering and unevenness of cell stacked in several layers which creates artifacts in the testing and data gathering capabilities for the infectious diseases and research community.

Ultraviolet devices are often benchmarked for efficacy of sanitizing and disinfection devices. Testing of ultraviolet disinfection devices determines the degree to which these devices can destroy or inactivate microorganisms and the results are generally given in terms of a percentage reduction of the microbial population or a log reduction of the population. The various testing, preparation methods and test protocols available to the world today are subject to wide variations in results due to the lack of standardization of the methods and experimental tools on the micron level. Implementations described by the present disclosure include a method to yield reproducible results of depositing a variable film of an inoculant containing one or more pathogens. Such results enable high precision assessments of disinfection methodologies/devices. In other words, health care facilities can leverage the implementations of the present disclosure to evaluate effective disinfection systems to combat the spread of disease and healthcare associated infections (HAIs). The implementations described in the present disclosure can be beneficial where disinfection is often expected for daily operation, such as the pharmaceutical industry, the food industry, and educational, commercial, and residential environments. Additionally, the disclosed implementations described in the present disclosure provide the ability to deposit microfilms on target surfaces where novel parameters have been developed to control aerodynamics, volumetric changes, as well as film composition, quantity, and density. These parameters have challenged the scientific community for years and limited the research and precision to evaluate microbial growth, therapeutic treatments, and critical scientific rate constants for the prediction of critical parameters for the world of decontamination and disinfection.

Health care facilities often disinfect equipment and surfaces in operating rooms, patient rooms and other areas after patients are discharged to reduce the risk of infection to patients and health care workers. Healthcare associated infections cost billions of dollars each year and can cause thousands of deaths. These facilities are expected to be equipped with the desirable disinfection systems. In this context, the ability to test and research microbiocidal activity on surfaces can be advantageous. Some implementations can be leveraged to advance scientific understanding of microbiocidal activity and improve disinfection technologies for public health.

While tests can be performed using manual methods and tools, such approaches suffer from large variability at the microscopic levels when inoculating microbes to surfaces such as glass slides, petri dishes, steel discs and other substrates. The variabilities in concentrations and layer formation can hinder accuracy and consistency of the deposition process. By way of background, clustering of spores and cells, also referred to as clumping, and, in water disinfection, as agglomeration or aggregation, provides increased resistance to ultraviolet disinfection. Clustering occurs when micro-organisms aggregate as a result of hydrophobicity, ionic surface charge and physical surface features. Cluster formation of a sample can be influenced by inoculant concentration, sample deposition method, sample spreading method, buffer solution, test medium and temperature.

In this context, the deposition of monolayers of bacteria and other microbes can provide a foundation for studying the aggregation and adhesion of pathogens such as bacteria to surfaces. For example, monolayers of spores can be created for use in biodosimetry to measure the biological response as a surrogate of radiation dose. For testing UV treatment, biodosimeters can be used to assess the ultraviolet dose directly instead of measuring the irradiance and computing the dose over time. In a biodosimetry study, the ability to create a desired target layer, for example, a monolayer, would be advantageous. Implementations described by the present disclosure allow adequate control procedures when manufacturing, for example, monolayers of an inoculant containing one or more pathogens. For example, these implementations can overcome the variability problem of clustered spores and cells by homogenous deposition.

The ability to deposit a monolayer or carefully structured levels of monolayers of microorganisms with precision control of the solution concentration and the concentration of cells on the target surface overcomes a significant barrier to the precision and reproducibility of experiments performed per a variety of testing methods and protocols. The limiting accuracy of many testing methods has been on the order of 99.9%. By way of background, UV disinfection data across the disinfectant industry thus far only has accurate rate constants for approximately 90% to 99.9% accuracy. The EPA standard for disinfection product, however, is a 99.9999% rate for disinfection outcome. For this reason alone, implementations of the present disclosure can allow the disinfectant industry to establish benchmark rate constants for high efficacy and reproducible testing under the EPA standard. A survival curve can plot the survival of a microbe under exposure to, for example, UV over time. Since the degree of this clustering depends on the test conditions, it is unpredictable and becomes a confounding artifact when comparing results from tests run under conditions where the degree of clustering and quantity of organisms was uncontrollable. The ability to deposit a desired monolayer in a reproducible manner allows for the measurement of reduction rates to a precision in excess of 99.9999%, or what is known as a six log reduction. This precision is, furthermore, achievable with implementations of the automated deposition system described by the present disclosure. This improvement represents a technological breakthrough for the infectious disease and public health community as well as ultraviolet disinfection industry, which heretofore been technically limited by the lack of performance measurement technology. Given the current and growing need for ultraviolet disinfection systems for healthcare and other industries, implementations described in the present disclosure provide a solution to the problem of controlling microfilm deposition for the development of these products.

It should be understood that the functional units or capabilities described in this specification may have been referred to or labeled as components or modules, in order to more particularly emphasize their implementation independence. Component or modules may be implemented in any combination of hardware circuits, programmable hardware devices, other discrete components. Components or modules may also be implemented in software for execution by various types of processors. An identified component or module of executable code may, for instance, comprise one or more physical or logical blocks of computer instructions, which may, for instance, be organized as an object, procedure, or function. Nevertheless, the executables of an identified component or module need not be physically located together, but may comprise disparate instructions stored in different locations which, when joined logically together, comprise the component or module and achieve the stated purpose for the component or module. Indeed, a component or module of executable code may be a single instruction, or many instructions, and may even be distributed over several different code segments, among different programs, and across several memory devices.

Similarly, operational data may be identified and illustrated herein within components or modules, and may be embodied in any suitable form and organized within any suitable type of data structure. The operational data may be collected as a single data set, or may be distributed over different locations including over different storage devices, and may exist, at least partially, merely as electronic signals on a system or network. The components or modules may be passive or active, including agents operable to perform desired functions.

Various implementations may address one or more of the problems and deficiencies discussed above. However, these implementations may additionally or alternatively prove useful in addressing other problems and deficiencies in a number of technical areas. Therefore, the scope of implementations of the present disclosure should not necessarily be construed as being limited to addressing any of the particular problems or deficiencies discussed herein, and are only limited by the scope of the claims.

While preferred configurations of the present disclosure have been shown and described herein, it will be obvious to those skilled in the art that such configurations are provided by way of example only. Numerous variations, changes, and substitutions will now occur to those skilled in the art without departing from the inventive concept of the disclosed implementations. It should be understood that various alternatives to the configurations described herein may be employed in practicing the inventive concept of the present disclosure. It is intended that the following claims define the scope of the inventive concept and that methods and structures within the scope of these claims and their equivalents be covered thereby.

The above detailed description includes references to the accompanying drawings, which form a part of the detailed description. The drawings show, by way of illustration, specific configurations. These configurations are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other configurations can be used, such as by one of ordinary skill in the art upon reviewing the above description. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed configuration. Thus, the following claims are hereby incorporated into the Detailed Description as examples or configurations, with each claim standing on its own as a separate configuration, and it is contemplated that such configurations can be combined with each other in various combinations or permutations. The scope of the inventive concept should be determined with reference to the appended claims, along with the full scope of equivalents to which such claims are entitled.

What is claimed is:

1. A system configured to automatically deposit a variable film of an inoculant containing one or more pathogens, the system comprising:
    a base;
    a removable chamber secured to the base, the removable chamber sized to contain a target surface disposed therein;
    a liquid inlet configured to provide the inoculant from a liquid inlet receiver to the removable chamber;
    a gas inlet configured to provide a pressurized gas from a gas tank to the removable chamber; and
    an adjustable nozzle configured to spray the inoculant from the liquid inlet and under the pressurized gas from the gas inlet onto the target surface within the removable chamber,
    wherein the removable chamber is mechanically adjustable in at least one volumetric dimension, and
    wherein the adjustable nozzle is movable relative to the removable chamber independent from the mechanical adjustment of the removable chamber.

2. The system of claim 1, wherein the base includes a control module configured to synchronize an opening of the liquid inlet and an opening of the gas inlet.

3. The system of claim 2, wherein the control module is further configured to control an amount of the inoculant to be sprayed in the removable chamber.

4. The system of claim 2, wherein the control module is further configured to control a pressure of the pressurized gas to be released that drive the inoculant from the liquid inlet to the removable chamber.

5. The system of claim 2, wherein the control module is further configured to control a spray radius of the adjustable nozzle.

6. The system of claim 2, wherein the control module is further configured to control a duration of spraying the inoculant from the adjustable nozzle.

7. The system of claim 2, wherein the control module is further configured to control an angle of spraying the inoculant from the adjustable nozzle.

8. The system of claim 2, wherein the control module is further configured to control a mixing ratio of the pressurized gas from the gas inlet and the inoculant from the liquid inlet.

9. The system of claim 2, wherein the control module is further configured to generate a set of control parameters based on a desired profile of the variable film to be deposited, and wherein the set of control parameters comprise at least one of: an amount of the inoculant to be sprayed, a pressure of the pressurized gas to be released, a spray radius, a spray duration, a spray angle, and a mixing ratio of the pressurized gas from the gas inlet and the inoculant from the liquid inlet.

10. The system of claim 1, wherein the removable chamber is configured to enclose the adjustable nozzle.

11. The system of claim 1, wherein the at least one volumetric dimension comprises one or more of: a height, a width, a length, or a radius.

12. The system of claim 1, further comprising:
    a controllable arm coupled to a top plate of the removable chamber, wherein the controllable arm is operable to adjust the at least one volumetric dimension of the removable chamber.

13. The system of claim 1, wherein the removable chamber is configured to receive one or more interchangeable stages holding at least one interchangeable insert for receiving the inoculant sprayed from the adjustable nozzle.

14. The system of claim 13, wherein the interchangeable insert is capable of receiving a target surface on which the variable film is deposited.

15. The system of claim 14, wherein the one or more interchangeable stages comprise a holding mechanism to hold the target surface.

16. The system of claim 10, wherein the removable chamber is sealed once connected to the base.

17. The system of claim 16, wherein the removable chamber is configured to receive one or more interchangeable stages through a bottom plate of the removable chamber.

18. The system of claim 16, wherein the removable chamber is configured to receive one or more interchangeable plates with at least one interchangeable insert through a bottom plate of the removable chamber.

19. The system of claim 16, wherein the removable chamber comprises a protective layer configured to encapsulate the removable chamber such that sprayed inoculant is limited to the removable chamber.

20. The system of claim 1, wherein the removable chamber includes a movable top plate, and wherein a volume of the removable chamber is adjustable by moving the top plate toward or away from the base.

21. The system of claim 20, further comprising a mounting plate movably coupled to the base, wherein the removable chamber is fixedly coupled to the mounting plate such that the removable chamber is vertically movable relative to the base.

22. The system of claim 21, further comprising an arm movably coupled to mounting plate, wherein the movable top plate is fixedly coupled to the arm such that the movable top plate is vertically movable relative to (i) a remainder of the removable chamber and (ii) the base.

23. The system of claim 22, wherein the nozzle is movably coupled to the arm such that the nozzle is movable up and down relative to (i) the movable top plate, (ii) the remainder of the removable chamber, and (iii) the base.

24. The system of claim 1, wherein the removable chamber and the adjustable nozzle are each movable relative to the base independent from each other.

25. The system of claim 1, further comprising a proximity sensor configured to generate data indicative of a position of the adjustable nozzle relative to the removable chamber, the target surface, or both.

26. The system of claim 25, wherein the proximity sensor is mounted on the adjustable nozzle.

27. The system of claim 25, wherein the proximity sensor is configured to generate data indicative of a distance between the adjustable nozzle and the target surface, a volume of the removable chamber, or both.

28. The system of claim 1, wherein the removable chamber is one of a plurality of removable chambers that each include a respective target surface, and wherein the adjustable nozzle is movable between the plurality of removable chambers and configured to spray the inoculant from the liquid inlet and under the pressurized gas from the gas inlet onto the respective target surface of each of the plurality of removable chambers.

29. A system for depositing an inoculant, the system comprising:
 a base;
 a mounting plate movably coupled to the base;
 a removable chamber fixedly coupled to the mounting plate such that the removable chamber is movable relative to the base, the removable chamber sized to contain a target surface disposed therein;
 an arm movably coupled to the removable chamber;
 a top plate fixedly coupled to the arm such that the top plate is movable relative to the removable chamber to thereby adjust a height of the removable chamber;
 an adjustable nozzle configured to spray the inoculant onto the target surface within the removable chamber, the adjustable nozzle movably coupled to the arm such that the adjustable nozzle is movable relative to the removable chamber independently from the top plate.

30. A system for depositing an inoculant, the system comprising:
 a base;
 a removable chamber coupled to the base, the removable chamber sized to contain a target surface disposed therein; and
 an adjustable nozzle configured to spray the inoculant onto the target surface within the removable chamber,
 wherein the removable chamber is mechanically adjustable in at least one volumetric dimension, and
 wherein the adjustable nozzle is movable relative to the removable chamber independent from the mechanical adjustment of the removable chamber.

* * * * *